(12) United States Patent
Jin et al.

(10) Patent No.: US 6,423,494 B1
(45) Date of Patent: Jul. 23, 2002

(54) DR6 AND USES THEREOF

(75) Inventors: Shengfang Jin, West Roxbury; Andrew W. Shyjan, Nahant; Christophe Van Huffel, Cambridge, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/470,175

(22) Filed: Dec. 22, 1999

Related U.S. Application Data

(62) Division of application No. 09/276,401, filed on Mar. 25, 1999.

(51) Int. Cl.$^7$ ............... C12Q 1/68; C12Q 1/00; C12Q 1/02; G01N 33/53; G01N 33/574
(52) U.S. Cl. ............... 435/6; 435/4; 435/7.1; 435/7.21; 435/7.23; 435/29; 435/30; 436/63; 436/64
(58) Field of Search ............... 435/4, 7.1, 7.21, 435/7.23, 6, 29, 30; 436/63, 64

(56) References Cited

PUBLICATIONS

Hill and Hosking. Differential effectiveness of a range of novel drug–resistance modulators, relative to verapamil, in influencing vinblastine or teniposide cytotoxicity in human lymphoblastoid CCRF–CEM sublines expressing classic or atypical multidrug resistance, 1994.*

Hill et al. Evaluation of S9788 as a potential modulator of drug resistance against human tumour sublined expressing differing resistance mechanisms in vitro. Int. J. Cancer 55(2):330–337, 1993.*

Kirchhausen, T., "Coated pits and coated vesicles—sorting it all out" Curr. Opin. in Structural Biol. 3:182–188, 1993.

Kirchhausen et al., "Linking cargo to vesicle formation: receptor tail interactions with coat proteins" Curr. Opin. in Cell Biol. 9(4):488–495, 1997.

Lee et al., GenBank Accession No. P35602, Oct. 1, 1994.

Nakayama et al., GenBank Accession No. P35585, Jun. 1, 1994.

* cited by examiner

*Primary Examiner*—Sheela Huff
*Assistant Examiner*—Alana M. Harris
(74) *Attorney, Agent, or Firm*—Fish & Richardson, P. C.

(57) ABSTRACT

Increased expression of DR6 is associated with drug resistance of certain cells (e.g., cancer cells). The invention provides methods for identifying drug resistant cells by measuring the expression or activity of DR6, methods for identifying modulators of drug resistance, and methods for modulating drug resistance by modulating the expression or activity of DR6.

15 Claims, 1 Drawing Sheet

GAATTCGGCACGAGGTACCAATCTGAAGTGGGAAGCGGCGCCGCCATCGCCTCCCGGCGCTCCCT
CCCCGACTCCTAAGTCCTTCGGCCGCCACCATGTCCGCCTCGGCTGTCTTCATTCTGGACGTTAA
GGGCAAGCCATTGATCAGCCGCAACTACAAGGGCGATGTGAGCAAGATTGAGCACTTCATGCCTT
TGCTGGTACAGCGGGAGGAGGAAGGCGCCCTGGCCCCGCTGCTGAGCCACGGCCAGGTCCACTTC
CTATGGATCAAACACAGCAACCTCTACTTGGTGGCCACCACATCGAAGAATGCCAATGCCTCCCT
GGTGTACTCCTTCCTGTATAAGACAATAGAGGTATTCTGCGAATACTTCAAGGAGCTGGAGGAGG
AGAGCATCCGGGACAACTTTGTCATCGTCTACGAGTTGCTGGACGAGCTCATGGACTTTGGCTTC
CCGCAGACCACCGACAGCAAGATCCTGCAGGAGTACATCACTCAGCAGAGCAACAAGCTGGAGAC
GGGCAAGTCACGGGTGCCACCCACTGTCACCAACGCTGTGTCCTGGCGCTCCGAGGGTATCAAGT
ATAAGAAGAACGAGGTCTTCATTGATGTCATAGAGTCTGTCAACCTGCTGGTCAATGCCAACGGC
AGCGTCCTTCTGAGCGAAATCGTCGGTACCATCAAGCTCAAGGTGTTTCTGTCGGGAATGCCAGA
GCTGCGGCTGGGCCTCAATGACCGCGTGCTCTTCGAGCTCACTGGCCGCAGCAAGAACAAATCAG
TAGAGCTGGAGGATGTAAAATTCCACCAGTGCGTGCGGCTCTCTCGCTTTGACAACGACCGCACC
ATCTCCTTCATCCCGCCTGATGGTGACTTTGAGCTCATGTCATACCGCCTCAGCACCCAGGTCAA
GCCACTGATCTGGATTGAGTCTGTCATTGAGAAGTTCTCCCACAGCCGCGTGGAGATCATGGTCA
AGGCCAAGGGGCAGTTTAAGAAACAGTCAGTGGCCAACGGTGTGGAGATATCTGTGCCTGTACCC
AGCGATGCCGACTCCCCCAGATTCAAGACCAGTGTGGGCAGCGCCAAGTATGTGCCGGAGAGAAA
CGTCGTGATTTGGAGTATTAAGTCTTTCCCGGGGGGCAAGGAGTACTTGATGCGAGCCCACTTTG
GCCTCCCCAGTGTGGAAAAGGAAGAGGTGGAGGGCCGGCCCCCCATCGGGGTCAAGTTTGAGATC
CCCTACTTCACCGTCTCTGGGATCCAGGTCCGATACATGAAGATCATTGAGAAAGTGGTTACCA
GGCCCTGCCCTGGGTTCGCTACATCACCCAGAGTGGCGATTACCAACTTCGTACCAGCTAGAAGG
GAGAAGAGATGGGGGCTTGAACACGGGGCTTCCTTACAGCCCCGGATGCAGATTTTAGAGGGAGG
GCAGGTGCGGGCTGTGTGTGTCTGTGTGAGGGCAGGTCCTGGACTTGGCAGTTTCTTGCTCCCAG
CACCCGCCCCTTCCTCACCTCTTCCTTATTCCATAGGCTGGGAGAGAAACTCTCTGCTTCCCTCG
CCCTTGGAGCTTTCCCCATCCCCCTGATTTTATATGAAGAAATAGAAGAGGGGCTTGAAGTCCCC
CTCGCGAGTGCCTTCTTGCAATTACCTGCCTTAGCGGGTGTTGCGGGTCCCTCCTTCACAGCCGC
TGAGCCCAGAGGTCCCGCTGGCCCCTCCTCTGAATTTTAGGATGTCATTAAAAAGATGAATCTAA
AAAAAAAAAAAAAAAAAAAAAAAAAAATTGGTGCGGCCGC

FIG. 1

MSASAVFILDVKGKPLISRNYKGDVSKIEHFMPLLVQREEEGALAPLLSHGQVHFLWIKHSNLYL
VATTSKNANASLVYSFLYKTIEVFCEYFKELEEESIRDNFVIVYELLDELMDFGFPQTTDSKILQ
EYITQQSNKLETGKSRVPPTVTNAVSWRSEGIKYKKNEVFIDVIESVNLLVNANGSVLLSEIVGT
IKLKVFLSGMPELRLGLNDRVLFELTGRSKNKSVELEDVKFHQCVRLSRFDNDRTISFIPPDGDF
ELMSYRLSTQVKPLIWIESVIEKFSHSRVEIMVKAKGQFKKQSVANGVEISVPVPSDADSPRFKT
SVGSAKYVPERNVVIWSIKSFPGGKEYLMRAHFGLPSVEKEEVEGRPPIGVKFEIPYFTVSGIQV
RYMKIIEKSGYQALPWVRYITQSGDYQLRTS

FIG. 2

DR6 AND USES THEREOF

RELATED APPLICATION INFORMATION

This application is a divisional of application Ser. No. 09/276,401, filed Mar. 25, 1999.

BACKGROUND OF THE INVENTION

The invention relates to chemotherapy and drug resistance.

Cancer chemotherapy commonly involves the administration of one or more cytotoxic or cytostatic drugs to a patient. The goal of chemotherapy is to eradicate a substantially clonal population (tumor) of transformed cells from the body of the individual, or to suppress or to attenuate growth of the tumor. Tumors may occur in solid or liquid form, the latter comprising a cell suspension in blood or other body fluid. A secondary goal of chemotherapy is stabilization (clinical management) of the afflicted individual's health status. Although the tumor may initially respond to chemotherapy, in many instances the initial chemotherapeutic treatment regimen becomes less effective or ceases to impede tumor growth. The selection pressure induced by chemotherapy promotes the development of phenotypic changes that allow tumor cells to resist the cytotoxic effects of a chemotherapeutic drug.

SUMMARY OF THE INVENTION

The present invention concerns DR6, a gene which is expressed at a relatively high level in a number of drug resistant cancer cell lines. DR6 nucleic acids and polypeptides are useful in, for example, diagnostic methods related to identification of drug resistant cells (e.g., cancer cells). DR6 nucleic acids and polypeptides are also useful in screening methods directed to the identification of compounds that can modulated (increase or decrease) the drug resistance of a particular cell type or multiple cell types.

The DR6 1792 nucleotide cDNA described below (SEQ ID NO:1) has a 1263 open reading frame (nucleotides 96 to 1358 of SEQ ID NO:1; SEQ ID NO:3) which encodes a 421 amino acid protein (SEQ ID NO:2).

The invention features a nucleic acid molecule which is at least 45% (or 55%, 65%, 75%, 85%, 95%, or 98%) identical to the nucleotide sequence shown in SEQ ID NO:1, SEQ ID NO:3, the nucleotide sequence of the cDNA insert of the plasmid deposited with ATCC as Accession Number (the "cDNA of ATCC PTA-1881"), or a complement thereof.

The invention features a nucleic acid molecule which includes a fragment of at least 15 (20, 25, 30, 150, 100, 150, 200, 250, 300, 350, 400, 450, 500, 550, 600, 650, 700, 800, 900, 1000, 1100, 1200 or 1266) nucleotides of the nucleotide sequence shown in SEQ ID NO:1, SEQ ID NO:3, the nucleotide sequence of the cDNA ATCC PTA-1881, or a complement thereof.

The invention features a nucleic acid molecule which includes a nucleotide sequence encoding a protein having an amino acid sequence that is at least 80% (or 82%, 85%, 95%, or 98%) identical to the amino acid sequence of SEQ ID NO:2, or the amino acid sequence encoded by the cDNA of ATCC PTA-1881.

In an embodiment, a DR6 nucleic acid molecule has the nucleotide sequence shown in SEQ ID NO:1, SEQ ID NO:3, or the nucleotide sequence of the cDNA of ATCC PTA-1881, or a complement thereof.

Also within the invention is a nucleic acid molecule which encodes a fragment of a polypeptide having the amino acid sequence of SEQ ID NO:2, the fragment including at least 15 (25, 30, 50, 100, 150, 200, 300, 400 or 421) contiguous amino acids of SEQ ID NO:2 or the polypeptide encoded by the cDNA of ATCC Accession Number PTA-1881.

The invention includes a nucleic acid molecule which encodes a naturally occurring allelic variant of a polypeptide comprising the amino acid sequence of SEQ ID NO:2 or the amino acid sequence encoded by the cDNA of ATCC Accession Number PTA-1881, wherein the nucleic acid molecule hybridizes to a nucleic acid molecule comprising SEQ ID NO:1 or SEQ ID NO:3 under highly (or moderately) stringent conditions.

In general, an allelic variant of a gene will be readily identifiable as mapping to the same chromosomal location as the gene. For example, in Example 1, the chromosomal location of the human DR6 is shown to be chromosome 19, position 41–43 cM, near marker stSG4364. Thus, allelic variants of human DR6 will be readily identifiable as mapping to the human DR6 locus on chromosome 19 near genetic marker stSG4364.

Also within the invention is an isolated DR6 protein having an amino acid sequence that is at least about 80% (82%, 85%, 95%, or 98%) identical to the amino acid sequence of SEQ ID NO:2. The amino acid sequence of such DR6 proteins can include one or more (e.g., 2, 5, 10, 15, 30, 25, 30 or more) conservative amino acid substitutions. For example, 1%, 2%, 3%, 5%, 7%, 10%, or 15% of the amino acid residues can be replaced by conservative substitution.

Also within the invention is an isolated DR6 protein which is encoded by a nucleic acid molecule having a nucleotide sequence that is at least about 65%, preferably 75%, 85%, or 95% identical to SEQ ID NO:3 or the protein coding portion of the cDNA of ATCC PTA-1881.

Also within the invention is a polypeptide which is a naturally occurring allelic variant of a polypeptide that includes the amino acid sequence of SEQ ID NO:2 or an amino acid sequence encoded by the cDNA insert of the plasmid deposited with ATCC as Accession Number PTA-1881, wherein the polypeptide is encoded by a nucleic acid molecule which hybridizes to a nucleic acid molecule comprising SEQ ID NO:1 or SEQ ID NO:3 under highly (or moderately) stringent conditions.

Another embodiment of the invention features DR6 nucleic acid molecules which specifically detect DR6 nucleic acid molecules. For example, in one embodiment, a DR6 nucleic acid molecule hybridizes under stringent conditions to a nucleic acid molecule comprising the nucleotide sequence of SEQ ID NO:1, SEQ ID NO:3, or the cDNA of ATCC PTA-1881, or a complement thereof. In another embodiment, the nucleic acid molecule is at least 15 (20, 25, 30, 150, 100, 150, 200, 250 300, 350, 400, 450, 500, 550, 600, 650, 700, 800, 900, 1000, 1100, 1200 or 1266) nucleotides in length and hybridizes under stringent conditions to a nucleic acid molecule comprising the nucleotide sequence shown in SEQ ID NO:1, SEQ ID NO:3, the cDNA of ATCC PTA-1881, or a complement thereof. In yet another embodiment, the invention provides an isolated nucleic acid molecule which is antisense to the coding strand of a DR6 nucleic acid.

Another aspect of the invention provides a vector, e.g., a recombinant expression vector, comprising a DR6 nucleic acid molecule of the invention. In another embodiment the invention provides a host cell containing such a vector or an isolated DR6 nucleic acid molecule. The invention also provides a method for producing DR6 protein by culturing, in a suitable medium, a host cell of the invention containing an isolated nucleic acid molecule or recombinant expression vector such that a DR6 protein is produced.

Another aspect of this invention features isolated or recombinant DR6 proteins and polypeptides. Preferred DR6 proteins and polypeptides possess at least one biological activity possessed by naturally occurring human DR6 protein, e.g., (1) the ability to form protein:protein interactions with membrane proteins; (2) the ability to form protein-protein interactions with a clatherin; (3) the ability to bind a DR6 ligand; (4) and the ability to increase drug resistance.

The DR6 proteins of the present invention, or biologically active portions thereof, can be operatively linked to a non-DR6 polypeptide (e.g., heterologous amino acid sequences) to form a DR6 fusion protein. The invention further features antibodies that specifically bind DR6 proteins, such as monoclonal or polyclonal antibodies. In addition, DR6 proteins or biologically active portions thereof can be incorporated into pharmaceutical compositions, which optionally include pharmaceutically acceptable carriers.

In another aspect, the present invention provides a method for detecting the presence of DR6 activity or expression in a biological sample by contacting the biological sample with an agent capable of detecting an indicator of DR6 activity such that the presence of DR6 activity is detected in the biological sample. For example, the invention includes a method for detecting the presence of a DR6 polypeptide in a sample. This method features the steps of contacting the sample with a compound which selectively binds to the polypeptide and then determining whether the compound binds to a polypeptide in the sample.

In some cases, the compound which binds to the polypeptide is an antibody. The invention also features methods for detecting the presence of a DR6 nucleic acid molecule in a sample. This method includes the steps of contacting the sample with a nucleic acid probe or primer which selectively hybridizes to a DR6 nucleic acid molecule (e.g., an mRNA encoding DR6); and then determining whether the nucleic acid probe or primer binds to a nucleic acid molecule in the sample.

In another aspect, the invention provides a method for modulating DR6 activity comprising contacting a cell with an agent that modulates (inhibits or stimulates) DR6 activity or expression such that DR6 activity or expression in the cell is modulated. In one embodiment, the agent is an antibody that specifically binds to DR6 protein. In another embodiment, the agent modulates expression of DR6 by modulating transcription of a DR6 gene, splicing of a DR6 mRNA, or translation of a DR6 mRNA. In yet another embodiment, the agent is a nucleic acid molecule having a nucleotide sequence that is antisense to the coding strand of the DR6 mRNA or the DR6 gene.

In one embodiment, the methods of the present invention are used to treat a subject having a disorder characterized by aberrant DR6 protein or nucleic acid expression or activity by administering an agent which is a DR6 modulator to the subject. In one embodiment, the DR6 modulator is a DR6 protein. In another embodiment the DR6 modulator is a DR6 nucleic acid molecule. In other embodiments, the DR6 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a DR6 protein; (ii) mis-regulation of a gene encoding a DR6 protein; (iii) aberrant RNA splicing; and (iv) aberrant post-translational modification of a DR6 protein, wherein a wild-type form of the gene encodes a protein with a DR6 activity.

The invention also features methods for identifying a compound which modulates the expression of DR6. In general, such methods entail measuring the expression of DR6 in the presence and absence of a teat compound and identifying those compounds which alter the expression of DR6.

Also within the invention are kits that include a compound which selectively binds to a DR6 polypeptide or nucleic acid and instructions for use. Such kits can be used to determine whether a particular cell type or cells within a biological sample, e.g., a sample of patient cells, are drug resistant.

The invention features methods for identifying a compound which binds to a DR6 polypeptide. These methods include the steps of contacting a DR6 polypeptide with a test compound and then determining whether the polypeptide binds to the test compound. In various embodiments of these methods, the binding of the test compound to the DR6 polypeptide is detected using an assay which measures binding of the test compound to the polypeptide or using a competition binding assay.

The invention also includes a method for modulating the activity of a DR6 polypeptide. This method includes the steps of contacting the polypeptide or a cell expressing the polypeptide with a compound which binds to the polypeptide in a sufficient concentration to modulate the activity of the polypeptide.

In another aspect, the invention provides a method for identifying a compound that modulates the activity of a DR6 polypeptide (e.g., a DR6 protein). In general, such methods entail measuring a biological activity of the polypeptide in the presence and absence of a test compound and identifying those compounds which alter the activity of the polypeptide. One such method includes the steps of contacting the polypeptide with a test compound and then determining the effect of the test compound on the activity of the polypeptide to thereby identify a compound which modulates the activity of the polypeptide.

Other aspects of the invention are methods and compositions relating to drug resistance. A "drug-resistant henotype" refers to a cellular phenotype which is associated with increased survival after exposure to a articular dose of a drug, e.g., a chemotherapeutic drug, compared to a cell that does not have this phenotype. A "drug-resistant cell" refers to a cell that exhibits this henotype. Drug resistance commonly occurs at multi-drug resistance (multiple drug resistance) in which a cell population or tumor becomes relatively resistance to a drug to which it has been exposed as well as to other drugs to which it has not been exposed.

Drug resistance can be characterized by lower intracellular concentration of a drug compared to a non-resistant cell or a less resistant cell as well as altered ability of a drug to affect its target compared to a non-resistant cell or a less resistant cell. Drug resistance is described in detail by Hochhauser and Harris ((1991) *Brit. Med. Bull.* 47:178–96); Simon and Schindler ((1994) *Proc. Nat'l Acad Sci USA* 91: 3497–504); and Harris and Hochhauser ((1992) *Acta Oncologica* 31:205–213); Scotto et.al. ((1986) *Science* 232: 751–55). Multi-drug resistance can be associated with, for example, altered composition of plasma membrane phospholipids; increased drug binding and intracellular accumulation; altered expression or activity of plasma membrane or endomembrane channels, transporters or translocators; altered rates of endocytosis and associated alteration in targeting of endosomes; altered exocytosis; altered intracellular ionic environments; altered expression or activity of proteins involved in drug detoxification; and altered expression or activity of proteins involved in DNA repair or replication.

Also within the invention is a method of determining whether a cell has a drug-resistant phenotype by measuring the expression (or activity) of DR6 in the cell and comparing this expression to that in a control cell. Increased expression (or activity) of DR6 in the cell compared to the Control cell indicates that the cell has a drug-resistant phenotype. In one embodiment of this method, DR6 expression is determined by measuring DR6 protein (e.g., measuring DR6 protein using an antibody directed against DR6). In another embodiment, DR6 expression is measured by quantifying mRNA encoding DR6 or the copy number of the DR6 gene. In another embodiment DR6 activity is measured using any assay which can quantify a biological activity of DR6.

The invention also includes a method for modulating the drug resistance of a cell by modulating DR6 expression or activity within the cell. Thus in one embodiment, the drug-resistance of a cell is reduced by contacting the cell with a molecule (e.g., an antisense nucleic acid molecule) that reduces the expression of DR6 within the cell.

Another aspect of the present invention is a method of improving effectiveness of chemotherapy for a mammal having a disorder associated with the presence of drug-resistant neoplastic cells. In this method, a chemotherapeutic drug and a molecule that reduces expression of DR6 can be co-administered to a mammal.

The invention also includes a method of identifying a compound that modulates the drug resistance of a cell by first contacting the cell with a test compound and then measuring and comparing DR6 expression in the cell exposed to the compound to DR6 expression in a control cell not exposed to the compound. The compound is identified as modulator of drug resistance when the level of DR6 expression in the cell exposed to the compound differs from the level of DR6 expression in cells not exposed to the compound. In one embodiment of this method, the cell has a drug-resistant phenotype. In another embodiment, the cell is a mammalian cell. This method may also include an optional step of measuring the drug resistance of the cell in the presence of the identified modulator of drug resistance. The DR6 modulating compounds that are identified in the foregoing methods are also included within the invention.

The invention also features a method of treating a mammal suspected of having a disorder associated with the presence of drug-resistant cells. This method includes the steps of determining whether a mammal has a disorder associated with the presence of drug-resistant cells having increased DR6 expression (e.g., drug-resistant cancer), and administering to the mammal a compound that sufficiently reduces the expression of DR6 so that the drug resistance of the cells associated with the disorder is modulated (i.e., reduced).

Another feature of the invention is a method for treating a patient having a neoplastic disorder (e.g., cancer) by administering to the patient a therapeutically effective amount of a compound that decreases the expression of DR6.

In the context of cancer treatment, the expression level of DR6 may be used to: 1) determine if a cancer, particularly a drug resistant cancer, can be treated by an agent or combination of agents; 2) determine if a cancer is responding to treatment with an agent or combination of agents; 3) select an appropriate agent or combination of agents for treating a cancer; 4) monitor the effectiveness of an ongoing treatment; and 5) identify new cancer treatments (either single agent or combination of agents). In particular, DR6 may be used as a marker (surrogate and/or direct) to determine appropriate therapy, to monitor clinical therapy and human trials of a drug being tested for efficacy and in developing new agents and therapeutic combinations.

Accordingly, the present invention provides methods for determining whether an agent, e.g., a chemotherapeutic agent such as doxorubicin or vinblastine, will be effective in reducing the growth rate of cancer cells comprising the steps of: a) obtaining a sample of cancer cells; b) determining the level of expression in the cancer cells of DR6; and c) identifying that an agent will be effective when DR6 is not expressed or is expressed at relatively low level. Alternatively, in step (c), an agent can be identified as being relatively ineffective when to use to treat the cancer when DR6 is expressed or is expressed at relatively high level.

As used herein, an agent is said to reduce the rate of growth of cancer cells when the agent can reduce at least 50%, preferably at least 75%, most preferably at least 95% of the growth of the cancer cells. Such inhibition can further include a reduction in survivability and an increase in the rate of death of the cancer cells. The amount of agent used for this determination will vary based on the agent selected. Typically, the amount will be a predefined therapeutic amount.

As used herein, an agent is defined broadly as anything that cancer cells can be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., Taxol, vinblastin and vincristine, alkylating agents, e.g., melphanlan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light. Preferred agents are doxorubicin and vinblastine.

The agents tested in the present methods can be a single agent or a combination of agents. For example, the present methods can be used to determine whether a single chemotherapeutic agent, such as methotrexate, can be used to treat a cancer or whether a combination of two or more agents can be used.

Cancer cells include, but are not limited to, carcinomas, such as squamous cell carcinoma, basal cell acarcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma.

The source of the cancer cells used in the methods of the invention will be based on how the method of the present invention is being used. For example, if the method is being used to determine whether a patient's cancer can be treated with an agent, or a combination of agents, then the preferred source of cancer cells will be cancer cells obtained from a cancer biopsy from the patient. Alternatively, cancer cells line of similar type to that being treated can be assayed. For example if breast cancer is being treated, then a breast cancer cell line can be used. If the method is being used to monitor the effectiveness of a therapeutic protocol, then a tissue sample from the patient being treated is the preferred source. If the method is being used to identify new therapeutic agents or combinations, then any cancer cells, e.g., cells of a cancer cell line, can be used.

A skilled artisan can readily select and obtain the appropriate cancer cells that are used in the present method. For cancer cell lines, sources such as The National Cancer Institute, for the NCI-60 cells used in the examples, are preferred. For cancer cells obtained from a patient, standard biopsy methods, such as a needle biopsy, can be employed.

In the methods of the present invention, the level or amount of expression of DR6 is determined. As used herein, the level or amount of expression refers to the absolute level of expression of an mRNA encoded by the gene or the absolute level of expression of the protein encoded by the gene (i.e., whether or not expression is or is not occurring in the cancer cells).

As an alternative to making determinations based on the absolute expression level of selected genes, determinations may be based on the normalized expression levels. Expression levels are normalized by correcting the absolute expression level of a sensitivity or resistance gene by comparing its expression to the expression of a gene that is not a sensitivity or resistance gene, e.g., a housekeeping genes that is constitutively expressed. Suitable genes for normalization include housekeeping genes such as the actin gene. This normalization allows one to compare the expression level in one sample, e.g., a patient sample, to another sample, e.g., a non-cancer sample, or between samples from different sources. Alternatively, the expression level can be provided as a relative expression level. To determine a relative expression level of a gene, the level of expression of the gene is determined for 10 or more samples, preferably 50 or more samples, prior to the determination of the expression level for the sample in question. The mean expression level of each of the gene assayed in the larger number of samples is determined and this is used as a baseline expression level for the gene in question. The expression level of the gene determined for the test sample (absolute level of expression) is then divided by the mean expression value obtained for that gene.

This provides a relative expression level and aids in identifying extreme cases of sensitivity or resistance.

Preferably, the samples used will be from similar tumors or from non-cancerous cells of the same tissue origin as the tumor in question. The choice of the cell source is dependent on the use of the relative expression level data. For example, using tumors of similar types for obtaining a mean expression score allows for the identification of extreme cases of sensitivity or resistance. Using expression found in normal tissues as a mean expression score aids in validating whether the gene assayed is tumor specific (versus normal cells).

Also within the invention is a method for increasing drug resistance in a cell having an undesirably low level of DR6 expression by administering a compound that increases the expression of DR6. Such methods are useful for the protection of non-neoplastic cells during chemotherapy.

The invention features a method for determining whether a test compound modulates the drug resistance of a cell, the method including: a) determining the level of DR6 expression (e.g., DR6 encoded by an endogenous or heterologous gene) in a cell in the presence of a test compound; b) determining the level of DR6 expression in the cell in the absence of the test compound; and c) identifying the compound as a modulator of drug resistance of the cell if the level of expression of DR6 in the cell in the presence of the best compound differs from the level of expression of DR6 in the cell in the absence of the test compound.

The invention also features a method for determining whether a test compound modulates the drug resistance of a cell, the method including: a) incubating DR6 protein in the presence of a test compound; b) determining whether the test compound binds to the DR6 protein; c) selecting a test compound which binds to the DR6 protein; d) administering the test compound selected in step c) to a non-human mammal having drug resistant cells; e) determining whether the test compound alters the drug resistance of the cells in the non-human mammal; and f) identifying the test compound as a modulator of drug resistance of the cell if the compound alters the drug resistance of the cells in step e).

The invention further features a method for determining whether a test cell has a drug-resistant phenotype, the method including: a) measuring the expression of DR6 in the test cell; b) comparing the expression of DR6 measured in step a) to the expression of DR6 in a control cell not having a drug-resistant phenotype; and c) determining that the test cell has a drug resistant phenotype if the expression of DR6 in the test cell is greater than the expression of DR6 in the control cell.

In another aspect the invention features a method of determining whether a test cell has a drug-resistant phenotype, the method including: a) measuring the activity of DR6 in the test cell; b) comparing the activity of DR6 measured in step a) to the activity of DR6 in a control cell not having a drug-resistant phenotype; and c) determining that the test cell has a drug resistant phenotype if the activity of DR6 in the test cell is greater than the activity of DR6 in the control cell.

In yet another aspect the invention features a method for determining whether a subject has or is at risk of developing a drug resistant tumor, the method including: a) measuring the expression of DR6 mRNA in a biological sample obtained from the subject (using, e.g., a nucleic acid molecule that hybridizes to DR6 mRNA); b) comparing the expression of DR6 mRNA measured in step a) to the expression of DR6 mRNA in a biological sample obtained from a control subject not having a drug resistant tumor; and c) determining that the patient has or is at risk of developing a drug resistant tumor if the expression of DR6 mRNA in the biological sample obtained from the patient is higher than the expression of DR6 mRNA in the biological sample obtained from the control subject.

In still another aspect the invention features a method for determining whether a subject has or is at risk of developing a drug resistant tumor, the method including: a) measuring the activity of DR6 in a biological sample obtained from the subject (using, e.g., an agent that binds to DR6 protein); b) comparing the activity of DR6 measured in step a) to the expression of DR6 mRNA in a biological sample obtained from a control subject not having a drug resistant tumor; and c) determining that the patient has or is at risk of developing a drug resistant tumor if the activity of DR6 in the biological sample obtained from the patient is higher than the activity of DR6 in the biological sample obtained from the control subject.

The invention also features a method for monitoring the effect of an anti-tumor treatment on a patient, the method including: a) measuring the expression of DR6 in a tumor sample obtained from the patient (using, e.g., a nucleic acid molecule that hybridizes to DR6 mRNA); b) comparing the expression of DR6 measured in step a) to the expression of DR6 in a control sample of cells; and c) determining that the anti-tumor treatment should be discontinued or modified if the expression of DR6 in the tumor sample is higher than the expression of DR6 in the control sample of cells.

The invention also features a method for monitoring the effect of an anti-tumor treatment on a patient, the method including: a) measuring the activity of DR6 in a tumor sample obtained from the patient (using, e.g., an agent that binds to DR6 protein); b) comparing the activity of DR6 measured in step a) to the activity of DR6 in a control sample of cells; and c) determining that the anti-tumor treatment should be discontinued or modified if the activity of DR6 in the tumor sample is higher than the activity of DR6 in the control sample of cells.

The invention further features a method for modulating the drug resistance of a cell by modulating DR6 expression within the cell and a method for reducing the drug resistance of cell by contacting the cell with a molecule which reduces the expression of DR6 within the cell.

The invention also features a method of increasing the effectiveness of a chemotherapeutic compound in a patient suffering from a disorder associated with the presence of drug-resistant neoplastic cells, the method including: a) administering a chemotherapeutic compound to the patient; and b) administering a compound with reduces DR6 expression to the patient.

The invention features a method of treating a mammal suspected of having a disorder associated with the presence of drug-resistant cells, the method including administering to the mammal a compound that reduces the expression of DR6 in the drug-resistant cells, the reduction be sufficient to reduce the drug resistance of the drug resistant cells and a method for increasing the drug resistance of cell that has an undesirably low level of DR6 expression, the method including exposing the cell to a compound that increases the expression of DR6.

The invention also features a method for treating a drug resistant tumor in a patient, the method comprising administering to said subject an amount of a MDA-9 antagonist effective to reduce drug resistance of said tumor in the patient. In another aspect, the invention features the use of an inhibitor of MDA-9 expression, or pharmaceutically acceptable salt thereof, or a pharmaceutical composition containing either entity, for the manufacture of a medicament for the treatment of a drug resistant tumor in a patient.

Unless otherwise defined, all technical and scientific terms used herein have the same meaning as commonly understood by one or ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, the materials, methods, and examples are illustrative only and are not intended to be limited. Other features and advantages of the invention will be apparent from the detailed description and from the claims.

BRIEF DESCRIPTION OF THE DRAWINGS

FIG. 1 is a depiction of the nucleotide sequence (SEQ ID NO:1) of a cDNA encoding human DR6. This cDNA encoding human DR6 includes an opening reading frame (SEQ ID NO:3) which extends from nucleotide 96 to nucleotide 1358 of SEQ ID NO: 1.

FIG. 2 is a depiction of the predicted amino acid sequence of human DR6 (SEQ ID NO:3).

DETAILED DESCRIPTION OF THE INVENTION

The nucleotide sequence of a cDNA encoding a human DR6 protein (SEQ ID NO:1) and the predicted amino acid sequence of human DR6 protein (SEQ ID NO:2) are shown in FIGS. 1 and 2 respectively. The open reading frame of the DR6 cDNA of FIG. 1 extends from nucleotide 96 to nucleotide 1358 of SEQ ID NO:1 (SEQ ID NO:3).

The association between DR6 expression and drug resistance was discovered during an analysis of genes that are relatively highly expressed in a number of drug resistant cell lines in the NCI60 cell line panel.

Various aspects of the invention are described in further detail in the following subsections.

I. Isolated Nucleic Acid Molecules

One aspect of the invention pertains to isolated nucleic acid molecules that encode DR6 proteins or biologically active portions thereof, as well as nucleic acid molecules sufficient for use as hybridization probes to identify DR6-encoding nucleic acids (e.g., DR6 mRNA) and fragments for use as PCR primers for the amplification or mutation of DR6 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic avid (i.e., sequences located at the 5' and 3' ends of the nucleic acid) in the genomic DNA of the organism from which the nucleic acid is derived. For example, in various embodiments, the isolated DR6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, the cDNA of ATCC PTA-1881, or a complement of any of these nucleotide sequences, can be isolated using standard molecular biology techniques and the sequence information provided herein. Using all or portion of the nucleic acid sequences of SEQ ID NO:1, SEQ ID NO:3, or the cDNA of ATCC PTA-1881, as a hybridization probe, DR6 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to DR6 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, or the cDNA of ATCC PTA-1881 or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding DR6, for example, a fragment which can be used as a probe or primer or a fragment encoding a biologically active portion of DR6. The nucleotide sequence determined from the cloning of the human DR6 gene allows for the generation of probes and primers designed for use in identifying and/or cloning DR6 homologues in other cell types, e.g., from other tissues, as well as DR6 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, the cDNA of ATCC PTA-1881 or of a naturally occurring mutant of SEQ ID NO:1, SEQ ID NO:3, or the cDNA of ATCC PTA-1881.

Probes based on the human DR6 nucleotide sequence can be used to detect transcripts or genomic sequences encoding the same or identical proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the DR6 protein of the present invention, identifying cells or tissue which mis-express DR6 protein, such as by measuring a level of a DR6-encoding nucleic acid in a sample of cells from a subject, e.g., detecting DR6 mRNA levels or determining whether a genomic DR6 gene has been mutated or deleted.

A nucleic acid fragment encoding a biologically active portion of DR6 can be prepared by isolating a portion of SEQ ID NO:1, SEQ ID NO:3, or the nucleotide sequence of the cDNA of ATCC PTA-1881 which encodes a polypeptide having a DR6 biological activity, expressing the encoded portion of DR6 protein (e.g., by recombinant expression in vitro) and assessing the activity of the encoded portion of DR6.

The invention further encompasses nucleic acid molecules that differ from the nucleotide sequence of SEQ ID NO:1, SEQ ID NO:3, the cDNA of ATCC PTA-1881 due to degeneracy of the genetic .ode and thus encode the same DR6 protein as that encoded by the nucleotide sequence shown in SEQ ID NO:1, SEQ ID NO:3, or the cDNA of ATCC PTA-1881.

In addition to the human DR6 nucleotide sequence shown in SEQ ID NO:1, SEQ ID NO:3, or the cDNA of ATCC PTA-1881, it will be appreciated by those skilled in the art that DNA sequence polymorphisms that lead to changes in the amino acid sequences of DR6 may exist within a population (e.g., the human population). Such genetic polymorphism in the DR6 gene may exist among individuals within a population due to natural allelic variation. As used herein, the terms "gene" and "recombinant gene" refer to nucleic acid molecules comprising an open reading frame encoding a DR6 protein, preferably a mammalian DR6 protein. Such natural allelic variations can typically result in 1–5% variance in the nucleotide sequence of the DR6 gene. Any and all such nucleotide variations and resulting amino acid polymorphisms in DR6 that are the result of natural allelic variation and that do not alter the functional activity of DR6 are intended to be within the scope of the invention.

Moreover, nucleic acid molecules encoding DR6 proteins from other species (DR6 orthologs/homologues), which have a nucleotide sequence which differs from that of a human DR6, are intended to be within the scope of the invention. Nucleic acid molecules corresponding to natural allelic variants and homologues of the DR6 cDNA of the invention can be isolated based on their identity to the human DR6 nucleic acid disclosed herein using the human cDNA, or a portion thereof, as a hybridization probe according to standard hybridization techniques under stringent hybridization conditions. In general, an allelic variant of a gene will be readily identifiable as mapping to the same chromosomal location as said gene.

The invention includes nucleic acid molecules which hybridize under highly stringent conditions or moderately stringent conditions to a selected nucleic acid molecule, e.g., a nucleic acid molecule having the nucleotide sequence of SEQ ID NO:1 or SEQ ID NO:3. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:., SEQ ID NO:3, the cDNA of ATCC PTA-1881 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the DR6 sequence that may exist in the population, the skilled artisan will further appreciate that changes can be introduced by mutation into the nucleotide sequence of SEQ ID NO:1, SEQ ID NO:3, the cDNA of ATCC PTA-1881, thereby leading to changes in the amino acid sequence of the encoded DR6 protein without altering the functional ability of the protein. For example, one can make nucleotide substitutions leading to amino acid substitutions at "non-essential" amino acid residues. A "non-essential" amino acid residue is a residue that can be altered from the wild-type sequence (e.g., the sequence of SEQ ID NO:2) without altering the biological activity, whereas an "essential" amino acid residue is required for biological activity. For example, amino acid residues that are conserved among the DR6 proteins of various species are predicted to be particularly unamenable to alteration.

Accordingly, another aspect of the invention pertains to nucleic acid molecules encoding DR6 proteins that contain changes in amino acid residues that are not essential for activity. Such DR6 proteins differ in amino acid sequence from SEQ ID NO:2 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2.

An isolated nucleic acid molecule encoding a DR6polypeptide can be created by introducing one or more nucleotide substitutions, additions or deletions into the nucleotide sequence of DR6 (SEQ ID NO:1, SEQ ID NO:3, the cDNA of ATCC PTA-1881) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in DR6 is preferably replaced with another amino acid residue from the same side chain family. Alternatively, mutations can be introduced randomly along all or part of a DR6 coding sequence, such as by saturation mutagenesis, and the resultant mutants can be screened for DR6 biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire DR6 coding strand, or to only a portion thereof, e.g., all or part of the protein coding region (or open reading frame). Am antisense nucleic acid molecule can be antisense to a noncoding region of the coding strand of a nucleotide sequence encoding DR6. The noncoding regions ("5' and 3' untranslated regions") are the 5' and 3' sequences which flank the coding region and are not translated into amino acids.

Given the coding strand sequences encoding DR6, antisense nucleic acids of the invention can be designed according to the rules of Watson and Crick base pairing. The antisense nucleic acid molecule can be complementary to the entire coding reason of DR6 mRNA, but more preferably is an oligonucleotide which is antisense to only a portion of the coding or noncoding region of the mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a DR6 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target Selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an -anomeric nucleic acid molecule. An -anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave DR6 mRNA transcripts to thereby inhibit translation of DR6 mRNA. A ribozyme having specificity for a DR6-encoding nucleic acid can be designed based upon the nucleotide sequence of DR6 cDNA disclosed herein. For example, a derivative of a Tetrahymena L-19 IVS RNA can be constructed in which the nucleotide sequence of the active site is complementary to the nucleotide sequence to be cleaved in a DR6-encoding mRNA. See, e.g., Cech et al. U.S. Pat. No. 4,987,071; and Cech et al. U.S. Pat. No. 5,116,742. Alternatively, DR6 mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, DR6 gene expression can be inhibited by targeting nucleotide sequences complementary to the regulatory region of the DR6 (e.g., the DR6 promoter and/or enhancers) to form triple helical structures that prevent transcription of the DR6 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93: 14670–675).

PNAs can be used for therapeutic and diagnostic applications. For example, PNAs can be used as antisense or antigene agents for sequence-specific modulation of gene expression by, e.g., inducing transcription or translation arrest or inhabiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of DR6 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of DR6 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1965) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated DR6 Proteins and Anti-DR6 Antibodies

One aspect of the invention pertains to isolated DR6 protein, and biologically active portions thereof, as well as polypeptide fragments suitable for use as immunogens to raise anti-DR6 antibodies. In one embodiment, native DR6 protein can be isolated from cells or tissue sources by an appropriate purification scheme using standard protein purification techniques. In another embodiment, DR6 proteins are produced by recombinant DNA techniques. Alternative to recombinant expression, a DR6-3 or DR6-4 protein or polypeptide can be synthesized chemically using standard peptide synthesis techniques.

An "isolated" or "purified" protein or biologically active portion thereof is substantially free of cellular material or other contaminating proteins from the cell or tissue source from which the DR6 protein is derived, or substantially free from chemical precursors or other chemicals when chemically synthesized. The language "substantially free of cellular material" includes preparations of DR6 protein in which the protein is separated from cellular components of the cells from which it is isolated or recombinantly produced. Thus, DR6 protein that is substantially free of cellular material includes preparations of DR6 protein having less than about 30%, 20%, 10%, or 5% (by dry weight) of non-DR6 protein (also referred to herein as a "contaminating protein"). When the DR6 protein or biologically active portion thereof is recombinantly produced, it is also preferably substantially free of culture medium, i.e., culture medium represents less than about 20%, 10%, or 5% of the volume of the protein preparation. When DR6 protein is produced by chemical synthesis, it is preferably substantially free of chemical precursors or other chemicals, i.e., it is separated from chemical precursors or other chemicals which are involved in the synthesis of the protein. Accordingly such preparations of DR6-3 or DR6-4 protein have less than about 30%, 20%, 10%, 5% (by dry weight) of chemical precursors or non-DR6 chemicals.

Biologically active portions of a DR6 protein include peptides comprising amino acid sequences sufficiently identical to or derived from the amino acid sequence of the DR6 protein (e.g., the amino acid sequence shown in SEQ ID NO:2), which include less amino acids than the full length DR6 protein, and exhibit at least one activity of DR6 protein. Typically, biologically active portions comprise a domain or motif with at least one activity of the DR6 protein. A biologically active portion of a DR6 protein can be a polypeptide which is, for example, 10, 25, 50, 100 or more amino acids in length. Preferred biologically active polypeptides include one or more identified DR6 structural domains.

Moreover, other biologically active portions, in which other regions of the protein are deleted, can be prepared by recombinant techniques and evaluated for one or more of the functional activities of a native DR6 protein.

DR6 protein has the amino acid sequence of SEQ ID NO:2. Other useful DR6 proteins are substantially identical to SEQ ID NO:2 and retain the functional activity of the protein of SEQ ID NO:2 yet differ in amino acid sequence due to natural allelic variation or mutagenesis. A useful DR6 protein is a protein which includes an amino acid sequence at least about 80%, preferably 82%, 85%, 95%, 98%, or 99% identical to the amino acid sequence of SEQ ID NO:2 and retains the functional activity of the DR6 protein of SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to DR6 nucleic acid molecules of the invention. BLAST protein searches can be performed with the XBLAST program, score=50, wordlength=3 to obtain amino acid sequences homologous to DR6 protein molecules of the invention. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See the Internet site at www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides DR6 chimeric or fusion proteins. As used herein, a DR6 "chimeric protein" or "fusion protein" comprises a DR6 polypeptide operatively linked to a non-DR6 polypeptide. A "DR6 polypeptide" refers to a polypeptide having an amino acid sequence corresponding to DR6, whereas a "non-DR6 polypeptide" refers to a polypeptide having an amino acid sequence corresponding to a protein which is not substantially identical to DR6, e.g., a protein which is different from the DR6 proteins and which is derived from the same or a different organism. Within a DR6 fusion protein, the DR6 polypeptide can correspond to all or a portion of a DR6 protein, preferably at least one biologically active portion of a DR6 protein. Within the fusion protein, the term "operatively linked" is intended to indicate that the DR6 polypeptide and the non-DR6 polypeptide are fused in-frame to each other. The non-DR6 polypeptide can be fused to the N-terminus or C-terminus of the DR6 polypeptide.

One useful fusion protein is a GST-DR6 fusion protein in which DR6 sequences are fused to the C-terminus of the GST sequences. Such fusion proteins can facilitate the purification of recombinant DR6.

In another embodiment, the fusion protein contains a signal sequence from another protein. In certain host cells (e.g., mammalian lost cells), expression and/or secretion of DR6 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.).

In yet another example, useful prokaryotic heterologous signal sequences include the phoA secretory signal (Molecular cloning, Sambrook et al, second edition, Cold spring harbor laboratory press, 1989; and the protein A secretory signal (Pharmacia Biotech; Piscataway, N.J.).

In yet another embodiment, the fusion protein is a DR6-immunoglobulin fusion protein in which all or part of DR6 is fused to sequences derived from a member of the immunoglobulin protein family. The DR6-immunoglobulin fusion proteins of the invention can be incorporated into pharmaceutical compositions and administered to a subject to inhibit an interaction between a DR6 ligand and DR6 protein. Inhibition of the DR6 ligand/DR6 interaction may be useful therapeutically for both the treatment of proliferative and differentiative disorders. Moreover, the DR6-immunoglobulin fusion proteins of the invention can be used as immunogens to produce anti-DR6 antibodies in a subject, to purify DR6 ligands and in screening assays to identify molecules which inhibit the interaction of DR6 with a DR6 ligand.

Preferably, a DR6 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: .9392). Moreover, many expression vectors are commercially available that already encode a fusion moiety (e.g., a GST polypeptide). A DR6-encoding nucleic acid can be cloned into such an expression vector such that the fusion moiety is linked in-frame to the DR6 protein.

The present invention also pertains to variants of DR6 protein which function as either DR6 agonists (mimetics) or as DR6 antagonists. Variants of the DR6 protein can be generated by mutagenesis, e.g., discrete point mutation or truncation of the DR-6 protein. An agonist of the DR6 protein can retain substantially the same, or a subset, of the biological activities of the naturally occurring form of the DR6 protein. An antagonist of the DR6 protein can inhibit one or more of the activities of the naturally occurring form of the DR6 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the DR6 protein.

Variants of the DR6 protein which function as either DR6 agonists (mimetics) or as DR6 antagonists can be identified by screening combinatorial libraries of mutants, e.g., truncation mutants, of the DR6 protein for DR6 protein agonist or antagonist activity. A library of DR6 variants can be produced by, for example, enzymatically ligating a mixture of synthetic oligonucleotides into gene sequences such that a degenerate set of potential DR6 sequences is expressible as individual polypeptides, or alternatively, as a set of larger fusion proteins (e.g., for phage display) containing the set of DR6 sequences therein. There are a variety of methods which can be used to produce libraries of potential DR6 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential DR6 sequences. Methods for synthesizing degenerate oligonucleotides are known in the art (see, e.g. Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the DR6 protein coding sequence can be used to generate a variegated population of DR6 fragments for screening and subsequent selection of variants of a DR6 protein. For example, a library of coding sequence fragments can be generated by treating a double stranded PCR fragment of a DR6 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the DR6 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of DR6 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify DR6 variants (Arkin and Yourvan (1992) *Proc. Natl. Acad. Sci. USA* 89:7811–7915; Delgrave et al. (1993) *Protein Engineering* 6(3):327–331).

An isolated DR6 protein, or a portion or fragment thereof, can be used as an immunogen to generate antibodies that bind DR6 using standard techniques for polyclonal and monoclonal antibody preparation. The full-length DR6 protein can be used or, alternatively, the invention provides antigenic peptide fragments of DR6 for use as immunogens. The antigenic peptide of DR6 comprises at least 8 (preferably 10, 15, 20, or 30) amino acid residues of the amino acid sequence shown in SEQ ID NO:2 and encompasses an epitope of DR6 such that an antibody raised against the peptide forms a specific immune complex with DR6.

Preferred epitopes encompassed by the antigenic peptide are regions of DR6 that are located on the surface of the protein, e.g , hydrophilic regions.

A DR6 immunogen typically is used to prepare antibodies by immunizing a suitable subject, (e.g., rabbit, goat, mouse or other mammal) with the immunogen. An appropriate immunogenic preparation can contain, for example, recombinantly expressed DR6 protein or a chemically synthesized DR6 polypeptide. The preparation can further include an adjuvant, such as Freund's complete or incomplete adjuvant, or similar immunostimulatory agent. Immunization of a suitable subject with an immunogenic DR6 preparation induces a polyclonal anti-DR6 antibody response.

Anti-DR6 antibodies are useful in the methods of the invention. The term antibody refers to immunoglobulin molecules and immunologically active portions of immunoglobulin molecules, i.e., molecules that contain an antigen binding site which specifically binds an antigen, such as DR6. A molecule which specifically binds to DR6 is a molecule which binds DR6, but does not substantially bind other molecules in a sample, e.g., a biological sample, which naturally contains DR6. Examples of immunologically active portions of immunoglobulin molecules include F(ab) and F(ab')$_2$ fragments which can be generated by treating the antibody with an enzyme such as pepsin. The term monoclonal antibody or monoclonal antibody composition refers to a population of antibody molecules that contain only one species of an antigen binding site capable of immunoreacting with a particular epitope of DR6. A monoclonal antibody composition thus typically displays a single binding affinity for a particular DR6 protein with which it immunoreacts.

Polyclonal anti-DR6 antibodies can be prepared as described above by immunizing a suitable subject with a DR6 immunogen. The anti-DR6 antibody titer in the immunized subject can be monitored over time by standard techniques, such as with an enzyme linked immunosorbent assay (ELISA) using immobilized DR6. If desired, the antibody molecules directed against DR6 can be isolated from the mammal (e.g., from the blood) and further purified by well-known techniques, such as protein A chromatography to obtain the IgG fraction. At an appropriate time after immunization, e.g., when the anti-DR6 antibody titers are highest, antibody-producing cells can be obtained from the subject and used to prepare monoclonal antibodies by standard techniques, such as the hybridoma technique originally described by Koller and Milstein (1975) *Nature* 256:495–497, the human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a DR6 immunogen as described above, and the culture supernatants of the resulting hybridoma cells are screened to identify a hybridoma producing a monoclonal antibody that binds DR6.

Any of the many well known protocols used for fusing lymphocytes and immortalized cell lines can be applied for the purpose of generating an anti-DR6 monoclonal antibody (see, e.g., Curent Protocols in Immunology, supra; Galfre et al. (1977) *Nature* 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387–402. Moreover, the ordinarily skilled worker will appreciate that there are many variations of such methods which also would be useful.

Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind DR6, e.g., using a standard ELISA assay.

Alternative to preparing monoclonal antibody-secreting hybridomas, a monoclonal anti-DR6 antibody can be identified and isolated by screening a recombinant combinatorial immunoglobulin library (e.g., an antibody phage display library) with DR6 to thereby isolate immunoglobulin library members that bind DR6. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734.

Additionally recombinant anti-DR6 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 1.39:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, (1985) *Science* 229:1202–1207; Oi et al. (1986) Bio/Techniques 4:214; U.S. Pat. 5,225,539; Jones et al. (1986) *Nature* 321:552–525; Verhoeyan et al. (1988) *Science* 239:1534; and Beidler et al. (1988) *J. Immunol.* 141:4053–4060.

An anti-DR6 antibody (e.g., monoclonal antibody) can be used to isolate DR6 by standard techniques, such as affinity chromatography or immunoprecipitation. An anti-DR6 antibody can facilitate the purification of natural DR6 from cells and of recombinantly produced DR6 expressed in host cells. Moreover, anti-DR6 antibody can be used to detect DR6 protein (e.g., in a cellular lysate or cell supernatant) in order to evaluate the abundance and pattern of expression of the DR6 protein. Anti-DR6 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, b-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding DR6 (or a portion thereof). A vector is a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors, e.g., viral vectors, replication defective retroviruses, adenoviruses and adeno-associated viruses).

Useful recombinant expression vectors comprise a DR6 nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. An expression vector can be introduced into host cells to thereby produce proteins or peptides, including fusion proteins or peptides, encoded by nucleic acids as described herein (e.g., DR6 proteins, mutant forms of DR6, fusion proteins, etc.).

The recombinant expression vectors of the invention can be designed for expression of DR6 in prokaryotic or eukaryotic cells, e.g., bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident l prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

An DR6 expression vector is a yeast expression vector. Examples of vectors for expression in yen be a *S. cerivisae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and picZ (InVitrogen Corp, San Diego, Calif.).

Alternatively, DR6 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

An DR6 nucleic acid can be expressed in mammalian cells using a mammalian expression vector. Examples of mammalian expression vectors include pCDM8 (Seed (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific prormoters (Calame and Eaton (1988) *Adv. Inmmunol.* 43:235–275), in particular promoters of T cell receptors (Winoto and Baltimore (1989) *EMBO J.* 8:729–733) and immunoglobulirs (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the a-fetoprotein promoter (Campes and Tilghman (1989) *Genes Dev.* 3:537–546).

Also useful in the methods of the invention are recombinant expression vectors comprising an DR6 nucleic acid molecule cloned into the expression vector in an antisense orientation. That is, the DNA molecule is operatively linked to a regulatory sequence in a manner which allows for expression (by transcription of the DNA molecule) of an RNA molecule which is antisense to DR6 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes See Weintraub et al., *Reviews—Trends in Genetics*, Vol. 1(1) 1986

Host cells into which an DR6 expression vector has been introduced are useful in certain metods of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A hosts cell can be any prokaryotic or eukaryotic cell. For example, DR6 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encodina DR6 or can be introduced on a separate vector. Cells stably transfected with the introduced nucleic acid can be identified by drug selection (e.g., cells that have incorporated the selectable marker gene will survive, while the other cells die).

A prokaryotic or eukaryotic host cell in culture can be used to produce (i.e., express) DR6 protein, e.g., by culturing the host cell (into which a recombinant expression vector encoding DR6 has been introduced) in a suitable medium such that DR6 protein is produced. DR6 ptoein can then be isolated from the medium or the host cell.

Host cells which are capable of expressing DR6 can also be used to produce nonhuman transgenic animals. For example, in one embodiment, a host cell of the invention is a fertilized oocyte or an embryonic stem cell into which DR6-coding sequences have been introduced. Such host cells can then be used to create non-human transgenic animals in which exogenous DR6 sequences have been introduced into their genome or homologous recombinant animals in which endogenous DR6 sequences have been altered. Such animals are useful for studying the function and/or activity of DR6 and for identifying and/or evaluating modulators of DR6 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous DR6 gene has been altered by homologous recombination between the endogenous gene and an exogenous DNA molecule introduced into a cell of the animal, e.g., an embryonic cell of the animal, prior to development of the animal.

A transgenic animal can be created by introducing DR6-encoding nucleic acid into the male pronuclei of a fertilized oocyte, e.g., by microinjection, retroviral infection, and allowing the oocyte to develop in a pseudopregnant female foster animal. The DR6 cDNA sequence e.g., that of SEQ ID NO:1 or SEQ ID NO:3 can be introduced as a transgene into the genome of a non-human animal. Alternatively, a non-human homologue of the human DR6 gene, such as a mouse DR6 gene, can be isolated based on hybridization to the human DR6 cDNA and used as a transgene. Intronic sequences and polyadenylation signals can also be included in the transgene to increase the efficiency of expression of the transgene. A tissue-specific regulatory sequence(s) can be operably linked to the DR6 transgene to direct expression of DR6 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the DR6 transgene in its genome and/or expression of DR6 mRNA in tissues or cells of the animals. A transgenic founder animal can then be used to breed additional animals carrying the transgene. Moreover, transgenic animals carrying a transgene encoding DR6 can further be bred to other transgenic animals carrying other transgenes.

To create an homologous recombinant animal, a vector is prepared which contains at least a portion of a DR6 gene (e.g., a human or a non-human homolog of the DR6 gene, e.g., a murine DR6 gene) into which a deletion, addition or substitution has been introduced to thereby alter, e.g., functionally disrupt, the DR6 gene. In a preferred embodiment, the vector is designed such that, upon homologous recombination, the endogenous DR6 gene is functionally disrupted (i.e., no longer encodes a functional protein; also referred to as a "knock out" vector). Alternatively, the vector can be designed such that, upon homologous recombination, the endogenous DR6 gene is mutated or otherwise altered but still encodes functional protein (e.g., the upstream regulatory region can be altered to thereby alter the expression of the endogenous DR6 protein).

In the homologous recombination vector, the altered portion of the DR6 gene is flanked at its 51 and 3' ends by additional nucleic acid of the DR6 gene to allow for homologous recombination to occur between the exogenous DR6 gene carried by the vector and an endogenous DR6 gene in an embryonic stem cell. The additional flanking DR6 nucleic acid is of sufficient length for successful homologous recombination with the endogenous gene. Typically, several kilobases of flanking DNA (both at the 5' and 3' ends) are included in the vector (see e.g., Thomas and Capecchi (1987) *Cell* 51:503 for a description of homologous recombination vectors). The vector is introduced into an embryonic stem cell line (e.g., by electroporation) and cells in which the introduced DR6 gene has homologously recombined with the endogenous DR6 gene are selected (see e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

Transgenic non-human animals can be produced which contain selected systems which allow for regulated expression of the trarsgene. One example of such a system is the cre/loxP recombinase system of bacteriophage P1. For a description of the cre/loxP recombinase system, see, e.g., Laksoet al. (1992) *Proc. Natl. Acad. Sci. USA* 89:6232–6236.

Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

DR6 proteins, and anti-DR6 antibodies, and modulators of DR6 expression or activity (also referred to herein as "active compounds") can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agent is such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by tile use of surfactants. Prevention of the action of microorganisms can be achieved by various antibacterial an antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and Uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

DR6 nucleic acid molecules of the invention can be inserted into vectors and used as gene therapy vectors. Gene therapy vectors can be delivered to a subject by, for example, intravenous injection, local administration (see U.S. Pat. 5,328,470) or by stereotactic injection (see e.g., Chen et al. ,1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The DR6 nucleic acid molecules, proteins, protein homologues, and antibodies described herein can be used in screening assays, predictive medicine (e.g., diagnostic assays, prognostic assays, monitoring clinical trials, and pharmacogenomics), and methods of treatment (e.g., therapeutic treatment methods and prophylactic treatment methods).

A. Screening Assays

The invention provides a method (also referred to herein as a "screening assay") for identifying modulators, i.e., candidate or test compounds or agents (e.g., peptides, peptidomimetics, small molecules or other drugs) which bind to DR6 proteins or have a stimulatory or inhibitory effect on, for example, DR6 expression or DR6 activity. Such identified compounds may be useful for the modulation of drug resistance.

In one embodiment, the invention provides assays for screening candidate or test compounds which bind to or modulate the activity of a DR6 protein or polypeptide or biologically active portion thereof. The test compounds of the present invention can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam, (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) J. Med. Chem. 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (Pat. Nos. 5,571,698; 5,403,484; and 5,223,409), plasmids (Cull et al. (1992) *Proc. Natl. Acad. Sci. USA* 89:1865–1865) or on phage (Scott and Smith (1990) *Science* 249:386–390; Devlin (1990) *Science* 249:404–406; Cwirla et al. (1990) *Proc. Natl. Acad. Sci.* 87:6378–6382; and Felici (1991) *J. Mol. Biol.* 222:301–310).

In one embodiment, an assay is a cell-based assay in which a cell which expresses a DR6 protein, or a biologically active portion thereof, is contacted with a test compound and the ability of the test compound to bind to a DR6 protein determined. The cell, for example, can be a yeast cell or a cell of mammalian origin. Determining the ability of the test compound to bind to the DR6 protein can be accomplished, for example, by coupling the test compound with a radioisotope or enzymatic label such that binding of the test compound to the DR6 protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting.

Alternatively, test compounds can be enzymatically labeled with, for example, horseradish peroxidase, alkaline phosphatase, or luciferase, and the enzymatic label detected by determination of conversion of an appropriate substrate to product. In a Preferred embodiment, the assay comprises contacting a cell which expresses a DR6 protein, or a biologically active portion thereof, with a known compound which binds DR6 to form an assay mixture, contacting the assay mixture with a test compound, and determining the ability of the test compound to interact with a DR6 protein, wherein determining the ability of the test compound to interact with a DR6 protein comprises determining the ability of the test compound to preferentially bind to DR6 or a biologically active portion thereof as compared to the known compound.

In another embodiment, an assay is a cell-based assay comprising contacting a cell expressing a DR6 protein, or a biologically active portion thereof, with a test compound and determining the ability of the test compound to modulate (e.g., stimulate or inhibit) the activity of the DR6 protein or biologically active portion thereof. Determining the ability of the test compound to modulate the activity of DR6 or a biologically active portion thereof can be accomplished, for example, by determining the ability of the DR6 protein to bind to or interact with a DR6 target molecule. As used herein, a "target molecule" is a molecule with which a DR6 protein binds or interacts in nature, for example, a molecule in the nucleus or cytoplasm of a cell which expresses a DR6 protein. A DR6 target molecule can be a non-DR6 molecule or a DR6 protein or polypeptide. The target, for example, can be a second intracellular protein which has catalytic activity, a protein which naturally binds to DR6, or a protein which facilitates the association of DNA with DR6.

Determining the ability of the DR6 protein to bind to or interact with a DR6 target molecule can be accomplished by one of the methods described above for determining direct binding. In a preferred embodiment, determining the ability of the DR6 protein to bind to or interact with a DR6 target molecule can be accomplished by determining the activity of the target molecule or detecting a cellular response, for example, cell survival or cell proliferation in the presence of a chemotherapeutic drug.

In yet another embodiment, an assay of the present invention is a cell-free assay comprising contacting a DR6 protein or biologically active portion thereof with a test compound and determining the ability of the test compound to bind to the DR6 protein or biologically active portion thereof. Binding of the test compound to the DR6 protein can be determined either directly or indirectly as described above. In a preferred embodiment, the assay includes contacting the DR6 protein or biologically active portion thereof with a known compound which binds DR6 to form an assay mixture, contacting the assay mixture with a test compound, and determining the ability of the test compound to interact with a DR6 protein, wherein determining the ability of the test compound to interact with a DR6 protein comprises determining the ability of the test compound to preferentially bind to DR6 or biologically active portion thereof as compared to the known compound.

In another embodiment, an assay is a cell-free assay comprising contacting DR6 protein or biologically active portion thereof with a test compound and determining the ability of the test compound to modulate (e.g., stimulate or inhibit) the activity of the DR6 protein or biologically active portion thereof. Determining the ability of the test compound to modulate the activity of DR6 can be accomplished, for example, by determining the ability of the DR6 protein to bind to a DR6 target molecule by one of the methods described above for determining direct binding. In an alternative embodiment, determining the ability of the test compound to modulate the activity of DR6 can be accomplished by determining the ability of the DR6 protein further modulate a DR6 target molecule. For example, the catalytic/enzymatic activity of the target molecule on an appropriate substrate can be determined as previously described.

In yet another embodiment, the cell-free assay comprises contacting the DR6 protein or biologically active portion thereof with a known compound which binds DR6 to form an assay mixture, contacting the assay mixture with a test compound, and determining the ability of the test compound to interact with a DR6 protein, wherein determining the ability of the test compound to interact with a DR6 protein comprises determining the ability of the DR6 protein to preferentially bind to or modulate the activity of a DR6 target molecule.

The cell-free assays of the present invention are amenable to use of both native and variant forms (e.g., peptide fragments and fusion proteins) of DR6. In the case of cell-free assays comprising a hydrophobic form of DR6, it may be desirable to utilize a solubilizing agent such that the hydrophobic form of DR6 is maintained in solution.

Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either DR6 or its target molecule to facilitate separation of complexed from uncomplexed forms of one or both of the proteins, as well as to accommodate automation of the assay.

Binding of a test compound to DR6, or interaction of DR6 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-tranfisferase/DR6 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or DR6 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of DR6 binding or activity determined using standard techniques.

Other techniques for immobilizing proteins on matrices can also be used in the screening assays of the invention. For example, either DR6 or its target molecule can be immobilized utilizing conjugation of biotin and streptavidin. Biotinylated DR6 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with DR6 or target molecules but which do not interfere with binding of the DR6 protein to its target molecule can be derivatized to the wells of the plate, and unbound target or DR6 trapped in the wells by antibody conjugation. Methods for detecting such complexes, in addition to those described above for the GST-immobilized complexes, include immunodetection of complexes using antibodies reactive with the DR6 or target molecule, as well as enzyme-linked assays which rely on detecting in enzymatic activity associated with the DR6 or target molecule.

In another embodiment, modulators of DR6 expression are identified in a method in which a cell is contacted with a candidate compound and the expression of DR6 (mRNA or protein, or the copy number of the DR6 gene) in the cell is determined. The level of expression of DR6 in the presence of the candidate compound is compared to the level of expression of DR6 in the absence of the candidate compound.

The candidate compound can then be identified as a modulator of DR6 expression based on this comparison. For example, when expression of DR6 mRNA or protein is greater (statistically significantly greater) in the presence of the candidate compound than in its absence, the candidate compound is identified as a stimulator of DR6 mRNA or protein expression. Alternatively, when expression of DR6 mRNA or protein is less (statistically significantly less) in the presence of the candidate compound than in its absence, the candidate compound is identified as an inhibitor of DR6 mRNA or protein expression. The level of DR6 mRNA or protein expression in the cells, or the number of DR6 gene copies per cell can be determined by methods described herein for detecting DR6 genomic DNA, mRNA, or protein.

DR6 proteins can be used as "bait proteins" in a two-hybrid assay or three hybrid assay (see, e.g., U.S. Pat. No. 5,283,317; Zervos et al. (1993) *Cell* 72:223–232; Madura et al (1993) *J. Biol. Chem.* 268:12046–12054; Bartel et al. (1993) *Bio/Techniques* 14:920–924; Iwabuchi et al. (1993) *Oncogene* 8:1693–1696; and WO94/10300), to identify other proteins, which bind to or interact with DR6 ("DR6-binding proteins" or "DR6-bp") and modulate DR6 activity. Such DR6-binding proteins are also likely to be involved in DNA damage repair or cellular resistance to chemotherapeutic drugs.

The two-hybrid system is based on the modular nature of most transcription factors, which consist of separable DNA-binding and activation domains. Briefly, the assay utilizes two different DNA constructs. In one construct, the gene that codes for DR6 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an DR6-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with DR6.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, DR6 nucleic acid molecules described herein or fragments thereof, can be used to map the location of DR6 genes on a chromosome. The mapping of the DR6 sequences to chromosomes is an important first step in correlating these sequences with genes associated with disease.

Briefly, DR6 genes can be mapped to chromosomes by preparing PCR primers (preferably 15–25 bp in length) from the DR6 sequences. Computer analysis of DR6 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the DR6 will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells car, the one human chromosome that contains the gene encoding, the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the DR6 sequences to design oligonucleotide primers, sublocalization can be achieved with panels of fragments from specific chromosomes. Other mapping strategies which can similarly be used to map a DR6 sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa.

A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verme et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., *Egeland* et al. (1987) *Nature*,325:783–787.

Moreover, differences in the DNA sequences between individuals affected and unaffected with a disease associated with the DR6 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The DR6 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the DR6 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue, The DR6 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding portions of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from DR6 sequences described herein is used to generate a unique identification database for an individual, those same reagents can later be used to identify tissue from that individual. Using the unique identification database, positive identification of the individual, living or dead, can be made from extremely small tissue samples.

3. Use of Partial DR6 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, are particularly appropriate for this use as greater numbers of polymorphisms occur in the noncoding regions, making it easier to differentiate individuals using this technique. Examples of polynucleotide reagents include the DR6 sequences or portions thereof, e.g., fragments derived from the noncoding regions of SEQ ID NO:1, which have a length of at least 20 or 30 bases.

The DR6-3 or DR6-4 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such DR6 probes can be used to identify tissue by species and/or by organ type.

In a similar fashion, these reagents, e.g., DR6 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining DR6 protein and/or nucleic acid expression as well as DR6 activity, in the context of a biological sample (e.g., blood, serum, cells, tissue) to thereby determine whether an individual is afflicted with a disease or disorder, or is at risk of developing a disorder, associated with aberrant DR6 expression or activity (e.g., altered drug resistance). The invention also provides for prognostic (or predictive) assays for determining whether an individual is at risk of developing a disorder associated with DR6 protein, nucleic acid expression or activity (e.g., altered drug resistance). For example, mutations in a DR6 gene can be assayed in a biological sample. Such assays can be used for prognostic or predictive purpose to thereby prophylactically treat an individual prior to the onset of a disorder characterized by or associated with DR6 protein, nucleic acid expression or activity. For example, because DR6 is expressed at a higher level in drug resistant cells (e.g., the doxorubicin resistant cell lines A2780, U937, and HL60 and the vinblastine cell line UCLA) than non-drug resistant cell lines, higher than normal expression of DR6 can be used as an indicator of drug resistance.

Another aspect of the invention provides methods for determining DR6 protein, nucleic acid expression or DR6 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of DR6 in clinical trials.

These and other agents are described in further detail in the following sections.

1. Diagnostic Assays

The invention provides a method of assessing expression, especially undesirable expression, of a cellular DR6 gene. Undesirable (e.g., excessive) expression may indicate the presence, persistence or reappearance of drug-resistant (e.g., vinblastine-resistant) tumor cells in an individual's tissue. More generally, aberrant expression may indicate the occurrence of a deleterious or disease-associated phenotype contributed to by DR6.

An exemplary method for detecting the presence or absence of DR6 in a biological sample involves obtaining a biological sample (preferably from a body site implicated in a possible diagnosis of diseased or malignant tissue) from a test subject and contacting the biological sample with a compound or an agent capable of detecting DR6 protein or nucleic acid (e.g., mRNA, genomic DNA) that encodes DR6 protein such that the presence of DR6 is detected in the biological sample. The presence and/or relative abundance of DR6 indicates aberrant or undesirable expression of a cellular DR6 gene, and correlates with the occurrence in situ of cells having a drug-resistant phenotype.

A preferred agent for detecting DR6 mRNA or genomic DNA is a labeled nucleic acid probe capable of hybridizing to DR6 mRNA or genomic DNA. The nucleic acid probe can be, for example, a full-length DR6 nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to DR6 mRNA or genomic DNA. Other suitable probes for use in the diagnostic assays of the invention are described herein.

A preferred agent for detecting DR6 protein is an antibody capable of binding to DR6 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect DR6 mRNA, protein, or genomic DNA in a biological sample in vitro as well as in vivo. For example, in vitro techniques for detection of DR6 mRNA include Northern hybridizations and in situ hybridizations. In vitro techniques for detection of DR6 protein include enzyme linked immunosorbent assays (ELISAs), Western blots, immunoprecipitations and immunofluorescence. In vitro techniques for detection of DR6 genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting DR6 protein, mRNA, or genomic DNA, such that the presence of DR6 protein, mRNA or genomic DNA is detected in the biological sample, and comparing the presence of DR6 protein, mRNA or genomic DNA in the control sample with the presence of DR6 protein, mRNA or genomic DNA in the test sample.

The invention also encompasses kits for detecting the presence of DR6 in a biological sample (a test sample). Such kits can be used to determine if a subject is suffering from or is at increased risk of developing a disorder associated with aberrant expression of DR6 (e.g., the presence of a drug resistance cancer). For example, the kit can comprise a labeled compound or agent capable of detecting DR6 protein or mRNA in a biological sample and means for determining the amount of DR6 in the sample (e.g., an anti-DR6 antibody or an oligonucleotide probe which binds to DNA encoding DR6, e.g., SEQ ID NO:1 or SEQ ID NO:3). Kits may also include instruction for observing that the tested subject is suffering from or is at risk of developing a disorder associated with aberrant expression of DR6 if the amount of DR6 protein or mRNA is above or below a normal level.

For antibody-based kits, the kit may comprise, for example: (1) a first antibody (e.g., attached to a solid support) which binds to DR6 protein; and, optionally, (2) a second, different antibody which binds to DR6 protein or the first antibody and is conjugated to a detectable agent.

For oligonucleotide-based kits, the kit may comprise, fox example: (1) a oligonucleotide, e.g., a detectably labeled oligonucleotide, which hybridizes to a DR6 nucleic acid sequence or (2) a pair of primers useful for amplifying a DR6 nucleic acid molecule;

The kit may also comprise, e.g., a buffering agent, a preservative, or a protein stabilizing agent. The kit may also comprise components necessary for detecting the detectable agent (e g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of DR6.

2. Prognostic Assays

The methods described herein can furthermore be utilized as diagnostic or prognostic assays to identify subjects having or at risk of developing a disease or disorder associated with aberrant DR6 expression or activity. For example, the assays described herein, such as the preceding diagnostic assays or the following assays, can be utilized to identify a subject having or at risk of developing a disorder associated with aberrant DR6 protein, nucleic acid expression or activity (e.g., the presence of drug resistant tumor cells).

Alternatively, the prognostic assays can be utilized to identify a subject having or at risk for developing such a disease or disorder. Thus, the present invention provides a method in which a test sample is obtained from a subject and DR6 protein or nucleic acid (e.g., mRNA, genomic DNA) is detected, wherein the presence or relative quantity of DR6 protein or nucleic acid is diagnostic for a subject having or at risk of developing a disease or disorder associated with aberrant DR6 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant DR6 expression or activity. Thus, if increased DR6 expression is a cause of increased drug resistance, such methods can be used to determine whether a subject can be effectively treated with a specific agent or class of agents (e.g., agents of a type which decrease DR6 activity). Thus, the present invention provides methods for determining whether a subject can be effectively treated with an agent for a disorder associated with aberrant DR6 expression or activity in which a test sample is obtained and DR6 protein or nucleic acid is detected (e.g., wherein the presence or relative quantity of DR6 protein or nucleic acid is diagnostic for a subject that can be administered the agent to treat a disorder associated with aberrant DR6 expression or activity). In some embodiments, the foregoing methods provide information useful in prognostication, staging and management of malignancies (tumors) that are characterized by altered expression of DR6 and thus by a drug-resistance phenotype. The information more specifically assists the clinician in designing chemotherapeutic or other treatment regimes to eradicate such malignancies from the body of an afflicted subject.

The methods of the invention can also be used to detect genetic lesions (e.g., mutations or amplifications) in a DR6 gene, thereby determining if a subject with the altered gene is at risk for a disorder characterized by aberrant cell proliferation and/or differentiation. For example, genetic mutations, whether of germline or somatic origin, may indicate whether the process of developing drug resistance has been initiated or is likely to arise in the tested cells. In preferred embodiments, the methods include detecting, in a sample of cells from the subject, the presence or absence of a genetic lesion characterized by at least one of an alteration affecting the integrity of a gene encoding a DR6-protein, the mis-expression of the DR6 gene, or the amplification of a DR6 gene. Preferably the sample of cells is obtained from a body tissue suspected of comprising transformed cells (e.g., cancer cells). Thus, the present method provides information relevant to diagnosis of the presence of a tumor.

Genetic lesions can be detected, for example, by ascertaining the existence of at least one of 1) a deletion of one or more nucleotides from a DR6 gene; 2) an addition of one or more nucleotides to a DR6 gene; 3) a substitution of one or more nucleotides of a DR6 gene, 4) a chromosomal rearrangement of a DR6 gene; 5) an alteration in the level of a messenger RNA transcript of a DR6 gene, 6) aberrant modification of a DR6 gene, such as of the methylation pattern of the genomic DNA, 7) the presence of a non-wild type splicing pattern of a messenger RNA transcript of a DR6 gene, 8) a non-wild type level of a DR6-protein, 9) allelic loss of a DR6 gene, 10) amplification of a DR6 gene, and 11) inappropriate post-translational modification of a DR6-protein. As described herein, there are a large number of assay techniques known in the art which can be used for detecting lesions in a DR6 gene. A preferred biological sample is a biopsy sample of tissue suspected of comprising transformed cells isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the DR6 gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a DR6 g4gene under conditions such that hybridization and amplification of the DR6-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a DR6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in DR6 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in DR6 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the DR6 gene and detect mutations by comparing the sequence of the sample DR6 with the corresponding wild-type (control) sequence. Additionally, sequencing of the DNA flanking the DR6 can be used to determine if the DR6 gene has been amplified. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the DR6 gene include methods in which protection from cleavage agents is used to detect mismatched bases in RNA/RNA or RNA/DNA heteroduplex,s (Myers et al. (1985) *Science* 230:1242). In general, the art technique of "mismatch cleavage" starts by providing heteroduplexes of formed by hybridizing (labeled) RNA or DNA containing the wild-type DR6 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with Si nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) *Proc. Natl Acad Sci USA* 85:4397; Saleeba et al (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs iii double-stranded DNA (so called "DNA mismatch repair" enzymes) in defined systems for detecting and mapping point mutations in DR6 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcirogenesis* 15:1657–1662). According to an exemplary embodiment, a probe based on a DR6 sequence, e.g., a wild-type DR6 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in DR6 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet Anal Tech Appl* 9:73–79). Single-stranded DNA fragments of sample and control DR6 nucleic acids will be denatured and allowed to renature. The secondary structure of single-stranded nucleic acids varies according to sequence, the resulting alteration in electrophoretic mobility enables the detection of even a single base change.

The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to Identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 31 end of one primer where, under appropriate conditions, mismatch can prevent, or reduce polynerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a DR6 gene.

Furthermore any cell type or tissue, preferably biopsy samples of tissue comprising or suspected of comprising transformed cells, in which DR6 is expressed may be utilized in the prognostic assays described herein.

3. Pharmacogenomics

Agents, or modulators which have a stimulatory or inhibitory effect on DR6 activity (e.g., DR6 gene expression) as identified by a screening assay described herein can be administered to individuals to treat (prophylactically or therapeutically) disorders (e.g., drug-resistance) associated with aberrant DR6 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of DR6 protein, expression of DR6 nucleic acid, or mutation content of DR6 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferse 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite in the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of DR6 protein, expression of DR6 nucleic acid, or mutation content of DR6 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, hen applied to dosing or drug selection, can avoid adverse reactions or therapeutic failure and thus enhance therapeutic or prophylactic efficiency when treating a subject with a DR6 modulator, such as a modulator identified by one of the exemplary screening assays described herein.

4. Monitoring of Effects During Clinical Trials

Monitoring the influence of agents (e.g., drugs, compounds) on the expression or activity of DR6 (e.g., the ability to modulate the drug-resistant phenotype of a cell) can be applied not only in basic drug screening, but also in clinical trials. For example, the effectiveness of an agent determined by a screening assay as described herein to decrease DR6 gene expression, protein levels, or downregulate DR6 activity, can be monitored in clinical trails of subjects exhibiting increased DR6 gene expression, protein levels, or upregulated DR6 activity.

Alternatively, the effectiveness of an agent determined by a screening assay to increase DR6 gene expression, protein levels, or upregulate DR6 activity (e.g., to increase the drug resistance of a non-cancerous cell), can be monitored in clinical trials of compounds designed to increase DR6 gene expression, protein levels, or upregulate DR6 activity. In such clinical trials, the expression or activity of DR6 and, preferably, other genes that have been implicated in, for example, a cellular proliferation disorder, can be used as a "read out" or markers of the drug resistance of a particular cell.

For example, and not by way of limitation, genes, including DR6, that are modulated in cells by treatment with an agent (e.g., compound, drug or small molecule) which modulates DR6 activity (e.g., identified in a screening assay as described herein) can be identified. Thus, to study the effect of agents on cellular proliferation disorders, for example, in a clinical trial, cells can be isolated and RNA prepared and analyzed for the levels of expression of DR6 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of DR6 or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a DR6 protein, mRNA, or genomic DNA in the preadministration sample; (iii) obtaining one or more post-administration samples from the subject; (iv) detecting the level of expression or activity of the DR6 protein, mRNA, or genomic DNA in the post-administration samples; (v) comparing the level of expression or activity of the DR6 protein, mRNA, or genomic DNA in the pre-administration sample with the DR6 protein, mRNA, or genomic DNA in the post administration sample or samples; and (vi) altering the administration of the agent to the subject accordingly. For example, increased administration of the agent may be desirable to decrease the expression or activity of DR6 to higher levels then detected, i.e., to increase the effectiveness of the agent.

D. Methods of Treatment

The present invention provides for both prophylactic and therapeutic methods of treating a subject at risk of (or susceptible to) a disorder or having a disorder associated with aberrant DR6 expression or activity. Such disorders include cellular resistance to chemotherapeutic drugs.

1. Prophylactic Methods

In one aspect, the invention provides a method for preventing in a subject, a disease or condition associated with an aberrant DR6 expression or activity (e.g., the development of drug resistance), by administering to the subject an agent which modulates DR6 expression or at least one DR6 activity. Subjects at risk for a condition which is caused or contributed to by aberrant DR6 expression or activity can be identified by, for example, any or a combination of diagnostic or prognostic assays as described herein. Administration of a prophylactic agent can occur prior to the manifestation of symptoms characteristic of the DR6 aberrancy, such that a disease or disorder is prevented or, alternatively, delayed in its progression. For example, administration of a prophylatic agent to a cancer patient may prevent or delay the development of drug resistance in the patient's cancer cells. Depending on the type of DR6 aberrancy, for example, a DR6 agonist or DR6 antagonist agent can be used for treating the subject. The appropriate agent can be determined based on screening assays described herein.

2. Therapeutic Methods

Another aspect of the invention pertains to methods of modulating DR6 expression or activity for therapeutic purposes. For example, the effectiveness of chemotherapy is "potentiated" (enhanced) by restoring or improving vulnerability of the transformed cells to the cytotoxic effects of a chemotherapeutic drug that otherwise would be less effective by reducing the expression of DR6 in the cells. The modulatory method of the invention involves contacting a cell with an agent that modulates one or more of the activities DR6 protein activity associated with the cell. An agent that modulates DR6 protein activity can be an agent as described herein, such as a nucleic acid or a protein, a naturally-occurring cognate ligand of a DR6 protein, a peptide, a DR6 peptidomimetic, or other small molecule. In one embodiment, the agent stimulates one or more of the biological activities of DR6 protein. Examples of such stimulatory agents include active DR6 protein and a nucleic acid molecule encoding DR6 that has been introduced into the cell. In another embodiment, the agent inhibits one or more of the biological activities of DR6 protein. Examples of such inhibitory agents include antisense DR6 nucleic acid molecules and anti-DR6 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a DR6 protein or nucleic acid molecule. In one embodiment, the method involves administering an agent (e.g., an agent identified by a screening assay described herein), or combination of agents that modulates (e.g., upregulates or downregulates) DR6 expression or activity. In another embodiment, the method involves administering a DR6 protein or nucleic acid molecule as therapy to compensate for reduced or aberrant DR6 expression or activity.

For example, in one embodiment, the method involves administering the desired drug (e.g., cyclophosphamide) to an individual afflicted with a drug-resistant cell population (a tumor, e.g., a carcinoma, sarcoma, leukemia, lymphoma, or lymphosarcoma), and coadministering an inhibitor of DR6 expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an DR6 antisense oligonucleotide in combination with one or more other antisense oligonucleotides) can be administered to the individual sufficiently in advance of administration of the chemotherapeutic drug to allow the antisense composition to permeate the individual's tissues, especially tissue comprising the transformed cells to be eradicated; to be internalized by transformed cells; and to disrupt DR6 gene expression and/or protein production.

Inhibition of DR6 activity is desirable in situations in which DR6 is abnormally upregulated and/or in which decreased DR6 activity is likely to have a beneficial effect. Conversely, stimulation of DR6 activity is desirable in situations in which DR6 is abnormally downregulated and/ or in which increased DR6 activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Isolation and Characterization of a Human DR6 cDNA

In order to identify genes involved in drug resistance, the expression various genes in drug resistant cancer cells was measured. The drug resistant cancer cell lines used were all members of the NCI60 panel of drug resistant cell lines. The cell lines in this panel are resistant to one or more chemotherapeutic compounds.

This expression analysis led to the identification of a cDNA (FIG. 1, SEQ ID NO:1) encoding DR6, a protein which appears to be related to C. elegans and mouse clathrin coat assembly protein AP47. Analysis of DR6 expression in the cell lines of the NCI60 panel revealed that increased DR6 expression is associated with resistance to chlorambucil, vinblastine, doxorubicin, etoposide, taxol, and topotecan, as well as other chemotherapeutic drugs.

The DR6 1794 nucleotide cDNA of FIG. 1 (SEQ ID NO:1) includes a 95 nucleotide 5' untranslated region, a 1263 nucleotide open reading frame (SEQ ID NO:3) encoding a 421 amino acid protein SEQ ID NO:2, and a 436 nucleotide 3' untranslated region. Human DR6 protein is predicted to have a molecule weight of 47.9 kD prior to post-translational modification.

Northern analysis of DR6 expression revealed that it is expressed in several colon cancer cell lines (Colo205, KM12, HCT-116, HCT15, HCC-2998, and HT29). This same analysis revealed that DR6 does not appear to be expressed in the colon cancer cell line SW-620. This cell line is relatively sensitive to cisplatin, doxorubicin, etoposide, topotecan, and chlorambucil.

The gene encoding DR6 mapped to chromosome 19 at 41–43 cM, near marker stSG4364.

Based on sequence homology, DR6 appears to be the human homolog of *C. elegans* clathrin coat assembly protein. At the amino acid level, human DR6 is 74.9% identical to *C. elegans* AP47 and 79.2% identical to murine AP47.

Clathrin coat assembly proteins bridge membrane receptors and clathrins and they are thought to be involved in protein sorting and membrane trafficking (Kirchhausen (1993) *Curr. Opin. Struct. Biol.* 3:182–88; and Kirchhausen et al. (1997) *Curr. Opin. Cell Biol.* (1997) 9:488–95). AP47 is thought to be located on golgi membrane. It is possible that human DR6 is located on golgi membrane and might be involved in intracellular vesicle trafficking and the detoxification of drugs through fusion with lysomal compartments.

Example 2

Preparation of DR6 Proteins

Recombinant DR6 can be produced in a variety of expression systems. For example, the mature DR6 peptide can be expressed as a recombinant glutathione-S-transferase (GST) fusion protein in *E. coli* and the fusion protein can be isolated and characterized. Specifically, as described above, DR6 can be fused to GST and this fusion protein can be expressed in *E. coli* strain PEB199. Expression of the GST-DR6 fusion protein in PEB199 can be induced with IPTG. The recombinant fusion protein can be purified from crude bacterial lysates of the induced PEB199 strain by affinity chromatography on glutathione beads.

A sample of *E. coli* harboring a plasmid (EpDR6) containing a cDNA encoding human DR6 was deposited with the American Type Culture Collection (ATCC), 10801 University Boulevard, Manassas, Va. 20110, on May 17, 2000, and assigned Accession Number PTA-1881. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining whether a test compound alters the expression of DR6 mRNA in a cell, the method comprising:
   a) measuring the level of DR6 mRNA in a sample comprising cells not exposed to the test compound;
   b) measuring the level of DR6 mRNA in a sample comprising cells exposed to the test compound; and
   c) determining that test compound alters the expression of DR6 mRNA when the level of DR6 mRNA measured in step a) differs from the level of DR6 mRNA measured in step b);
   wherein the DR6 mRNA is selected from the group consisting of:
   i) an mRNA comprising the nucleotide sequence of SEQ ID NO:3 wherein each T is replaced by a U;
   ii) an mRNA encoding the amino acid sequence of SEQ ID NO:2; and
   iii) an mRNA comprising the coding sequence of the cDNA insert of plasmid epDR6 deposited with the ATCC® as Accession No. PTA-1881 wherein each T is replaced by a U.

2. The method of claim 1 wherein the cells comprise in vitro cultured cells.

3. The method of claim 1 wherein the cells are obtained from a patient biopsy.

4. The method of claim 3 wherein the cells are obtained from a biopsy of a colon tumor.

5. The method of claim 3 wherein the cells are obtained from a biopsy of normal colon tissue.

6. The method of claim 1 wherein the cells are exposed to the test compound in vivo.

7. The method of claim 1 wherein the cells are exposed to the test compound in vitro.

8. The method of claim 1 wherein the cells are transfected with a nucleic acid molecule comprising a constitutively expressed gene encoding a polypeptide comprising the amino acid sequence of SEQ ID NO:2.

9. The method of claim 2 wherein the in vitro cultured cells comprises cells of a colon cancer cell line.

10. The method of claim 3 wherein the patient biopsy is obtained from a patient that has undergone chemotherapy.

11. The method of claim 3 wherein the patient biopsy is obtained from a patient that has not undergone chemotherapy.

12. The method of claim 1 wherein the sample comprises cells exposed to the test compound and the sample comprising cells not exposed to the test compound comprise cells exposed to a selected chemotherapeutic drug.

13. The method of claim 12 wherein the chemotherapeutic drug is selected from the group consisting of chlorambucil, vinblastine, doxorubicin, etoposide, taxol, and topotecan.

14. The method of claim 1 wherein steps a) and b) further comprise isolating mRNA from the cells and contacting the isolated mRNA with a nucleic acid molecule comprising a nucleotide sequence comprising at least 15 contiguous nucleotides of SEQ ID NO:1.

15. The method of claim 2 wherein steps a) and b) comprise isolating polypeptides from the cells and contacting the isolated polypeptides with an antibody that selectively binds to the DR6 polypeptide.

* * * * *

SEQUENCE LISTING

```
<160> NUMBER OF SEQ ID NOS:  3

<210> SEQ ID NO 1
<211> LENGTH: 1796
<212> TYPE: DNA
<213> ORGANISM: Homo sapiens
<220> FEATURE:
<221> NAME/KEY: CDS
<222> LOCATION: (96)...(1358)

<400> SEQUENCE: 1
gaattcggca cgaggtacca atctgaagtg ggaagcggcg ccgccatcgc ctcccggcgc        60
tccctccccg actcctaagt ccttcggccg ccacc atg tcc gcc tcg gct gtc       113
                                       Met Ser Ala Ser Ala Val
                                         1               5 ttc att ctg gac gtt aag ggc aag cca ttg atc agc cgc aac tac aag        161
Phe Ile Leu Asp Val Lys Gly Lys Pro Leu Ile Ser Arg Asn Tyr Lys
            10                  15                  20 ggc gat gtg agc aag att gag cac ttc atg cct ttg ctg gta cag cgg        209
Gly Asp Val Ser Lys Ile Glu His Phe Met Pro Leu Leu Val Gln Arg
         25                  30                  35 gag gag gaa ggc gcc ctg gcc ccg ctg ctg agc cac ggc cag gtc cac        257
Glu Glu Glu Gly Ala Leu Ala Pro Leu Leu Ser His Gly Gln Val His
     40                  45                  50 ttc cta tgg atc aaa cac agc aac ctc tac ttg gtg gcc acc aca tcg        305
Phe Leu Trp Ile Lys His Ser Asn Leu Tyr Leu Val Ala Thr Thr Ser
 55                  60                  65                  70 aag aat gcc aat gcc tcc ctg gtg tac tcc ttc ctg tat aag aca ata        353
Lys Asn Ala Asn Ala Ser Leu Val Tyr Ser Phe Leu Tyr Lys Thr Ile
                 75                  80                  85
```

```
gag gta ttc tgc gaa tac ttc aag gag ctg gag gag gag agc atc cgg      401
Glu Val Phe Cys Glu Tyr Phe Lys Glu Leu Glu Glu Glu Ser Ile Arg
             90                  95                 100 gac aac ttt gtc atc gtc tac gag ttg ctg gac gag ctc atg gac ttt      449
Asp Asn Phe Val Ile Val Tyr Glu Leu Leu Asp Glu Leu Met Asp Phe
            105                 110                 115 ggc ttc ccg cag acc acc gac agc aag atc ctg cag gag tac atc act      497
Gly Phe Pro Gln Thr Thr Asp Ser Lys Ile Leu Gln Glu Tyr Ile Thr
    120                 125                 130 cag cag agc aac aag ctg gag acg ggc aag tca cgg gtg cca ccc act      545
Gln Gln Ser Asn Lys Leu Glu Thr Gly Lys Ser Arg Val Pro Pro Thr
135                 140                 145                 150 gtc acc aac gct gtg tcc tgg cgc tcc gag ggt atc aag tat aag aag      593
Val Thr Asn Ala Val Ser Trp Arg Ser Glu Gly Ile Lys Tyr Lys Lys
                155                 160                 165 aac gag gtc ttc att gat gtc ata gag tct gtc aac ctg ctg gtc aat      641
Asn Glu Val Phe Ile Asp Val Ile Glu Ser Val Asn Leu Leu Val Asn
            170                 175                 180 gcc aac ggc agc gtc ctt ctg agc gaa atc gtc ggt acc atc aag ctc      689
Ala Asn Gly Ser Val Leu Leu Ser Glu Ile Val Gly Thr Ile Lys Leu
    185                 190                 195 aag gtg ttt ctg tcg gga atg cca gag ctg cgg ctg ggc ctc aat gac      737
Lys Val Phe Leu Ser Gly Met Pro Glu Leu Arg Leu Gly Leu Asn Asp
200                 205                 210 cgc gtg ctc ttc gag ctc act ggc cgc agc aag aac aaa tca gta gag      785
Arg Val Leu Phe Glu Leu Thr Gly Arg Ser Lys Asn Lys Ser Val Glu
215                 220                 225                 230 ctg gag gat gta aaa ttc cac cag tgc gtg cgg ctc tct cgc ttt gac      833
Leu Glu Asp Val Lys Phe His Gln Cys Val Arg Leu Ser Arg Phe Asp
                235                 240                 245 aac gac cgc acc atc tcc ttc atc ccg cct gat ggt gac ttt gag ctc      881
Asn Asp Arg Thr Ile Ser Phe Ile Pro Pro Asp Gly Asp Phe Glu Leu
            250                 255                 260 atg tca tac cgc ctc agc acc cag gtc aag cca ctg atc tgg att gag      929
Met Ser Tyr Arg Leu Ser Thr Gln Val Lys Pro Leu Ile Trp Ile Glu
    265                 270                 275 tct gtc att gag aag ttc tcc cac agc cgc gtg gag atc atg gtc aag      977
Ser Val Ile Glu Lys Phe Ser His Ser Arg Val Glu Ile Met Val Lys
280                 285                 290 gcc aag ggg cag ttt aag aaa cag tca gtg gcc aac ggt gtg gag ata     1025
Ala Lys Gly Gln Phe Lys Lys Gln Ser Val Ala Asn Gly Val Glu Ile
295                 300                 305                 310 tct gtg cct gta ccc agc gat gcc gac tcc ccc aga ttc aag acc agt     1073
Ser Val Pro Val Pro Ser Asp Ala Asp Ser Pro Arg Phe Lys Thr Ser
                315                 320                 325 gtg ggc agc gcc aag tat gtg ccg gag aga aac gtc gtg att tgg agt     1121
Val Gly Ser Ala Lys Tyr Val Pro Glu Arg Asn Val Val Ile Trp Ser
            330                 335                 340 att aag tct ttc ccg ggg ggc aag gag tac ttg atg cga gcc cac ttt     1169
Ile Lys Ser Phe Pro Gly Gly Lys Glu Tyr Leu Met Arg Ala His Phe
    345                 350                 355 ggc ctc ccc agt gtg gaa aag gaa gag gtg gag ggc cgg ccc ccc atc     1217
Gly Leu Pro Ser Val Glu Lys Glu Glu Val Glu Gly Arg Pro Pro Ile
360                 365                 370 ggg gtc aag ttt gag atc ccc tac ttc acc gtc tct ggg atc cag gtc     1265
Gly Val Lys Phe Glu Ile Pro Tyr Phe Thr Val Ser Gly Ile Gln Val
375                 380                 385                 390 cga tac atg aag atc att gag aaa agt ggt tac cag gcc ctg ccc tgg     1313
Arg Tyr Met Lys Ile Ile Glu Lys Ser Gly Tyr Gln Ala Leu Pro Trp
                395                 400                 405
```

-continued

```
gtt cgc tac atc acc cag agt ggc gat tac caa ctt cgt acc agc        1358
Val Arg Tyr Ile Thr Gln Ser Gly Asp Tyr Gln Leu Arg Thr Ser
        410                 415                 420 tagaagggag aagagatggg ggcttgaaca cggggcttcc ttacagcccc ggatgcagat   1418
tttagaggga gggcaggtgc gggctgtgtg tgtctgtgtg agggcaggtc ctggacttgg   1478
cagtttcttg ctcccagcac ccgccccttc ctcacctctt ccttattcca taggctggga   1538
gagaaactct ctgcttccct cgccttgga gctttcccca tcccctgat tttatatgaa    1598 gaaatagaag aggggcttga agtccccctc gcgagtgcct tcttgcaatt acctgcctta  1658
gcgggtgttg cgggtccctc cttcacagcc gctgagccca gaggtcccgc tggcccctcc  1718
tctgaatttt aggatgtcat taaaaagatg aatctaaaaa aaaaaaaaaa aaaaaaaaa   1778 aaaaattggt gcggccgc                                                 1796
```

<210> SEQ ID NO 2
<211> LENGTH: 421
<212> TYPE: PRT
<213> ORGANISM: Homo sapiens

<400> SEQUENCE: 2

```
Met Ser Ala Ser Ala Val Phe Ile Leu Asp Val Lys Gly Lys Pro Leu
 1               5                  10                  15

Ile Ser Arg Asn Tyr Lys Gly Asp Val Ser Lys Ile Glu His Phe Met
                20                  25                  30

Pro Leu Leu Val Gln Arg Glu Glu Gly Ala Leu Ala Pro Leu Leu
         35                  40                  45

Ser His Gly Gln Val His Phe Leu Trp Ile Lys His Ser Asn Leu Tyr
     50                  55                  60

Leu Val Ala Thr Thr Ser Lys Asn Ala Asn Ala Ser Leu Val Tyr Ser
 65                  70                  75                  80

Phe Leu Tyr Lys Thr Ile Glu Val Phe Cys Glu Tyr Phe Lys Glu Leu
                 85                  90                  95

Glu Glu Glu Ser Ile Arg Asp Asn Phe Val Ile Val Tyr Glu Leu Leu
            100                 105                 110

Asp Glu Leu Met Asp Phe Gly Phe Pro Gln Thr Thr Asp Ser Lys Ile
        115                 120                 125

Leu Gln Glu Tyr Ile Thr Gln Gln Ser Asn Lys Leu Glu Thr Gly Lys
    130                 135                 140

Ser Arg Val Pro Pro Thr Val Thr Asn Ala Val Ser Trp Arg Ser Glu
145                 150                 155                 160

Gly Ile Lys Tyr Lys Lys Asn Glu Val Phe Ile Asp Val Ile Glu Ser
                165                 170                 175

Val Asn Leu Leu Val Asn Ala Asn Gly Ser Val Leu Leu Ser Glu Ile
            180                 185                 190

Val Gly Thr Ile Lys Leu Lys Val Phe Leu Ser Gly Met Pro Glu Leu
        195                 200                 205

Arg Leu Gly Leu Asn Asp Arg Val Leu Phe Glu Leu Thr Gly Arg Ser
    210                 215                 220

Lys Asn Lys Ser Val Glu Leu Glu Asp Val Lys Phe His Gln Cys Val
225                 230                 235                 240

Arg Leu Ser Arg Phe Asp Asn Asp Arg Thr Ile Ser Phe Ile Pro Pro
                245                 250                 255

Asp Gly Asp Phe Glu Leu Met Ser Tyr Arg Leu Ser Thr Gln Val Lys
            260                 265                 270
```

```
Pro Leu Ile Trp Ile Glu Ser Val Ile Glu Lys Phe Ser His Ser Arg
        275                 280                 285
Val Glu Ile Met Val Lys Ala Lys Gly Gln Phe Lys Lys Gln Ser Val
        290                 295                 300
Ala Asn Gly Val Glu Ile Ser Val Pro Val Pro Ser Asp Ala Asp Ser
305                 310                 315                 320
Pro Arg Phe Lys Thr Ser Val Gly Ser Ala Lys Tyr Val Pro Glu Arg
                325                 330                 335
Asn Val Val Ile Trp Ser Ile Lys Ser Phe Pro Gly Gly Lys Glu Tyr
            340                 345                 350
Leu Met Arg Ala His Phe Gly Leu Pro Ser Val Glu Lys Glu Glu Val
        355                 360                 365
Glu Gly Arg Pro Pro Ile Gly Val Lys Phe Glu Ile Pro Tyr Phe Thr
    370                 375                 380
Val Ser Gly Ile Gln Val Arg Tyr Met Lys Ile Ile Glu Lys Ser Gly
385                 390                 395                 400
Tyr Gln Ala Leu Pro Trp Val Arg Tyr Ile Thr Gln Ser Gly Asp Tyr
                405                 410                 415
Gln Leu Arg Thr Ser
            420

<210> SEQ ID NO 3
<211> LENGTH: 1266
<212> TYPE: DNA
<213> ORGANISM: Homo sapiens

<400> SEQUENCE: 3
atgtccgcct cggctgtctt cattctggac gttaagggca agccattgat cagccgcaac        60
tacaagggcg atgtgagcaa gattgagcac ttcatgcctt gctggtaca gcggaggag         120 gaaggcgccc tggccccgct gctgagccac ggccaggtcc acttcctatg atcaaacac        180 agcaacctct acttggtggc caccacatcg aagaatgcca atgcctccct ggtgtactcc        240
ttcctgtata gacaataga ggtattctgc gaatacttca aggagctgga ggaggagagc        300
atccgggaca ctttgtcat cgtctacgag ttgctggacg agctcatgga ctttggcttc        360
ccgcagacca ccgacagcaa gatcctgcag gagtacatca ctcagcagag caacaagctg        420
gagacgggca gtcacgggt gccacccact gtcaccaacg ctgtgtcctg gcgctccgag        480
ggtatcaagt ataagaagaa cgaggtcttc attgatgtca tagagtctgt caacctgctg        540
gtcaatgcca acggcagcgt ccttctgagc gaaatcgtcg gtaccatcaa gctcaaggtg        600
tttctgtcgg gaatgccaga gctgcggctg ggcctcaatg accgcgtgct cttcgagctc        660
actggccgca gcaagaacaa atcagtagag ctggaggatg taaaattcca ccagtgcgtg        720
cggctctctc gctttgacaa cgaccgcacc atctccttca tcccgcctga tggtgacttt        780
gagctcatgt cataccgcct cagcacccag gtcaagccac tgatctggat tgagtctgtc        840
attgagaagt tctcccacag ccgcgtggag atcatggtca aggccaaggg gcagtttaag        900
aaacagtcag tggccaacgg tgtggagata tctgtgcctg tacccagcga tgccgactcc        960
cccagattca agaccagtgt gggcagcgcc aagtatgtgc cggagagaaa cgtcgtgatt      1020
tggagtatta gtctttccc gggggggcaag gagtacttga tgcgagccca ctttggcctc      1080
cccagtgtgg aaaaggaaga ggtggagggc cggcccccca tcggggtcaa gtttgagatc      1140
ccctacttca ccgtctctgg gatccaggtc cgatacatga agatcattga gaaaagtggt      1200
```

| | |
|---|---|
| taccaggccc tgccctgggt tcgctacatc acccagagtg gcgattacca acttcgtacc | 1260 |
| agctag | 1266 |